United States Patent
Barber, III et al.

(10) Patent No.: US 11,166,415 B2
(45) Date of Patent: Nov. 9, 2021

(54) PLANT GROWTH WITH RADIATION-BASED MILDEW AND/OR BACTERIA CONTROL

(71) Applicant: Sensor Electronic Technology, Inc., Columbia, SC (US)

(72) Inventors: Arthur Peter Barber, III, Lexington, SC (US); Alexander Dobrinsky, Silver Spring, MD (US); Maxim S. Shatalov, Columbia, SC (US); Michael Shur, Vienna, VA (US)

(73) Assignee: Sensor Electronic Technology, Inc., Columbia, SC (US)

( * ) Notice: Subject to any disclaimer, the term of this patent is extended or adjusted under 35 U.S.C. 154(b) by 34 days.

(21) Appl. No.: 16/205,896

(22) Filed: Nov. 30, 2018

(65) Prior Publication Data

US 2019/0098842 A1    Apr. 4, 2019

Related U.S. Application Data

(63) Continuation-in-part of application No. 15/659,192, filed on Jul. 25, 2017, now Pat. No. 10,624,978.

(Continued)

(51) Int. Cl.
*F26B 3/34* (2006.01)
*A01G 7/06* (2006.01)
(Continued)

(52) U.S. Cl.
CPC .............. *A01G 7/06* (2013.01); *A01G 7/045* (2013.01); *A01G 9/246* (2013.01); *A61L 2/0047* (2013.01);

(Continued)

(58) Field of Classification Search
CPC . A01G 7/06; A01G 7/045; A01G 7/00; A01G 9/246; A61L 2/24; A61L 2/0052;
(Continued)

(56) References Cited

U.S. PATENT DOCUMENTS 7,553,456 B2   6/2009  Gaska et al.
7,634,996 B2   12/2009 Gaska et al.
(Continued)

FOREIGN PATENT DOCUMENTS

JP    200922175 A    2/2009

OTHER PUBLICATIONS

Mccormack, J., U.S. Appl. No. 15/659,192, Office Action 1, dated Apr. 1, 2019, 16 pages.

(Continued)

*Primary Examiner* — John P McCormack
(74) *Attorney, Agent, or Firm* — LaBatt, LLC

(57) ABSTRACT

A solution for controlling mildew in a cultivated area is described. The solution can include a set of ultraviolet sources that are configured to emit ultraviolet and/or blue-ultraviolet radiation to harm mildew present on a plant or ground surface. A set of sensors can be utilized to acquire plant data for at least one plant surface of a plant, which can be processed to determine a presence of mildew on the at least one plant surface. Additional features can be included to further affect the growth environment for the plant. A feedback process can be implemented to improve one or more aspects of the growth environment.

20 Claims, 12 Drawing Sheets

Related U.S. Application Data

(60) Provisional application No. 62/592,569, filed on Nov. 30, 2017, provisional application No. 62/366,682, filed on Jul. 26, 2016.

(51) Int. Cl.

| | | |
|---|---|---|
| *A61L 2/24* | (2006.01) | |
| *A61L 2/00* | (2006.01) | |
| *A01G 7/04* | (2006.01) | |
| *A01G 9/24* | (2006.01) | |
| *A01G 7/00* | (2006.01) | |

(52) U.S. Cl.
CPC ........... *A61L 2/0052* (2013.01); *A61L 2/0058* (2013.01); *A61L 2/0076* (2013.01); *A61L 2/24* (2013.01); *A01G 7/00* (2013.01); *A61L 2202/11* (2013.01); *A61L 2202/14* (2013.01); *A61L 2202/16* (2013.01)

(58) Field of Classification Search
CPC .... A61L 2/0058; A61L 2/0076; A61L 2/0047; A61L 2202/16; A61L 2202/11; A61L 2202/14
USPC .......................................................... 34/275
See application file for complete search history.

(56) References Cited

U.S. PATENT DOCUMENTS

| | | | |
|---|---|---|---|
| 8,084,394 B2 | 12/2011 | Steffen | |
| 8,277,734 B2 | 10/2012 | Koudymov et al. | |
| 8,384,047 B2 | 2/2013 | Shur et al. | |
| 8,980,178 B2 | 3/2015 | Gaska et al. | |
| 9,006,680 B2 | 4/2015 | Bettles et al. | |
| 9,034,271 B2 | 5/2015 | Shur et al. | |
| 9,061,082 B2 | 6/2015 | Gaska et al. | |
| 9,138,499 B2 | 9/2015 | Bettles et al. | |
| 9,179,703 B2 | 11/2015 | Shur et al. | |
| 9,550,004 B2 | 1/2017 | Smetona et al. | |
| 9,572,903 B2 | 2/2017 | Dobrinsky et al. | |
| 9,603,960 B2 | 3/2017 | Dobrinsky et al. | |
| 9,687,577 B2 | 6/2017 | Dobrinsky et al. | |
| 9,707,307 B2 | 7/2017 | Shur et al. | |
| 9,718,706 B2 | 8/2017 | Smetona et al. | |
| 9,724,441 B2 | 8/2017 | Shur et al. | |
| 9,750,830 B2 | 9/2017 | Shur et al. | |
| 9,757,486 B2 | 9/2017 | Dobrinsky et al. | |
| 9,795,699 B2 | 10/2017 | Shur et al. | |
| 9,801,965 B2 | 10/2017 | Bettles et al. | |
| 9,802,840 B2 | 10/2017 | Shturm et al. | |
| 9,878,061 B2 | 1/2018 | Shur et al. | |
| 9,919,068 B2 | 3/2018 | Shur et al. | |
| 9,974,877 B2 | 5/2018 | Bettles et al. | |
| 9,981,051 B2 | 5/2018 | Shur et al. | |
| 9,987,383 B2 | 6/2018 | Bilenko et al. | |
| 9,999,782 B2 | 6/2018 | Shur et al. | |
| 10,004,821 B2 | 6/2018 | Dobrinsky et al. | |
| 10,021,838 B1 | 7/2018 | Gustafik | |
| 10,040,699 B2 | 8/2018 | Smetona et al. | |
| 10,099,944 B2 | 10/2018 | Smetona et al. | |
| 10,624,978 B2 | 4/2020 | Dobrinsky et al. | |
| 2003/0082072 A1 | 5/2003 | Koji et al. | |
| 2005/0072935 A1* | 4/2005 | Lussier | G01N 21/6456 250/458.1 |
| 2009/0272029 A1 | 11/2009 | Aiking et al. | |
| 2010/0042234 A1 | 2/2010 | May et al. | |
| 2010/0193707 A1 | 8/2010 | Yamada et al. | |
| 2011/0163246 A1 | 7/2011 | Ishiwata et al. | |
| 2013/0048545 A1 | 2/2013 | Shatalov et al. | |
| 2014/0060094 A1 | 3/2014 | Shur et al. | |
| 2014/0060096 A1 | 3/2014 | Shur et al. | |
| 2014/0060104 A1 | 3/2014 | Shur et al. | |
| 2014/0202962 A1 | 7/2014 | Bilenko et al. | |
| 2014/0250778 A1 | 9/2014 | Suntych | |
| 2015/0069270 A1* | 3/2015 | Shur | A23L 3/28 250/492.1 |
| 2015/0165079 A1 | 6/2015 | Shur et al. | |
| 2015/0359915 A1* | 12/2015 | Farren | A61L 2/24 422/24 |
| 2016/0007544 A1 | 1/2016 | Takashima et al. | |
| 2016/0114186 A1 | 4/2016 | Dobrinsky et al. | |
| 2017/0057842 A1 | 3/2017 | Dobrinsky et al. | |
| 2017/0100495 A1 | 4/2017 | Shur et al. | |
| 2017/0100496 A1 | 4/2017 | Shur et al. | |
| 2017/0189711 A1 | 7/2017 | Shur et al. | |
| 2017/0245527 A1 | 8/2017 | Dobrinsky et al. | |
| 2017/0245616 A1 | 8/2017 | Lakios et al. | |
| 2017/0281812 A1 | 10/2017 | Dobrinsky et al. | |
| 2017/0290934 A1 | 10/2017 | Dobrinsky et al. | |
| 2017/0368215 A1 | 12/2017 | Shatalov et al. | |
| 2018/0028700 A1 | 2/2018 | Dobrinsky et al. | |
| 2018/0092308 A1 | 4/2018 | Dobrinsky et al. | |
| 2018/0104368 A1 | 4/2018 | Dobrinsky et al. | |
| 2018/0117194 A1 | 5/2018 | Dobrinsky et al. | |
| 2018/0185529 A1 | 7/2018 | Shur et al. | |
| 2018/0221521 A1 | 8/2018 | Shur et al. | |
| 2018/0243458 A1 | 8/2018 | Shatalov et al. | |
| 2018/0339075 A1 | 11/2018 | Kennedy et al. | |
| 2019/0030477 A1 | 1/2019 | Shatalov | |
| 2019/0099613 A1 | 4/2019 | Estes et al. | |
| 2019/0100445 A1 | 4/2019 | Dobrinsky | |
| 2019/0100718 A1 | 4/2019 | Estes et al. | |
| 2019/0117811 A1 | 4/2019 | Barber, III | |
| 2019/0125907 A1 | 5/2019 | Dobrinsky | |
| 2019/0135659 A1 | 5/2019 | Smetona et al. | |

OTHER PUBLICATIONS

MCCormack, J., U.S. Appl. No. 15/659,192, Final Office Action 1, dated Sep. 30, 2019, 6 pages.

International Application No. PCT/US2017/043896, International Search Report and Written Opinion, dated Jan. 31, 2018, 13 pages.

"Bellow, S. et al., ""Optical detection of downy mildew in grapevineleaves: daily kinetics of autofluorescence upon infection,"" Journal of Experimental Botany, 2012, vol. 64, No. 1, 11 pages. "

Application No. 17835185.4, Search Report, dated Feb. 11, 2020, 10 pages.

McCormack, J., U.S. Appl. No. 15/659,192, Notice of Allowance, dated Dec. 16, 2019, 7 pages.

Japanese Application No. 2019-503655, Notice of Allowance, dated Oct. 13, 2020, 3 pages, no English translation.

Office Action, European Application No. 17835185.4, dated Apr. 30, 2021, 7 pages.

\* cited by examiner

FIG. 8A

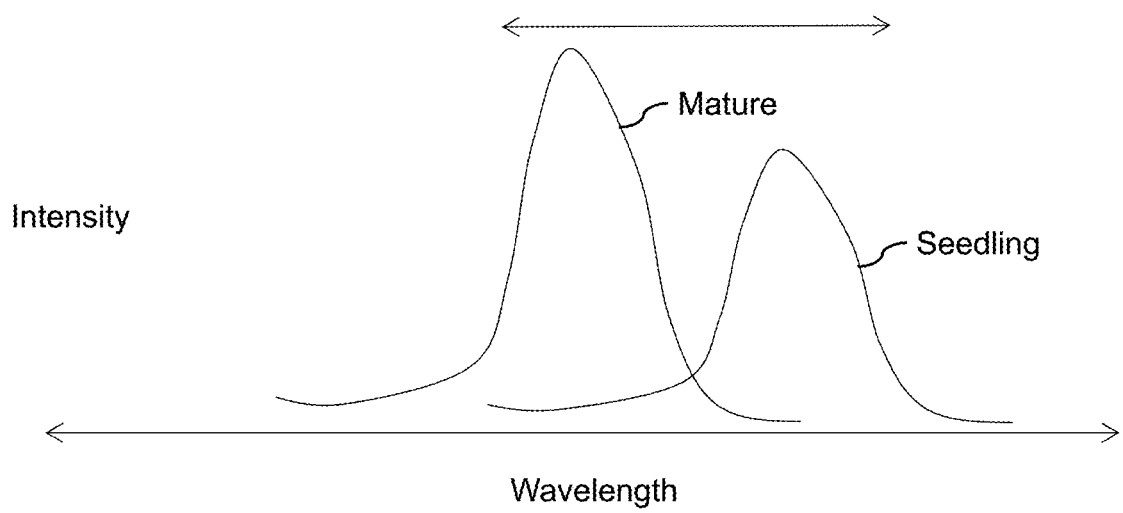

FIG. 8B

| | |
|---|---|
| 275 nanometers | Mildew control |
| 280 nanometers | Encourage growth |
| 285 nanometers | Increase yield, shorten seedling growth time |
| 295 nanometers | Mature plants, increase antioxidants, increase vitamin D (mushrooms), increase THC & CBD (Cannabis), extend post-harvest shelf life |
| 385 nanometers | Increase color in flowers/crops, increase flavor, reduce use of pesticides |
| 400 nanometers | Increase color in flowers/crops, increase flavor, increase aroma |

PLANT GROWTH WITH RADIATION-BASED MILDEW AND/OR BACTERIA CONTROL

REFERENCE TO RELATED APPLICATIONS

The current application claims the benefit of U.S. Provisional Application No. 62/592,569, filed 30 Nov. 2017, and is a continuation-in-part of U.S. Utility patent application Ser. No. 15/659,192, filed on 25 Jul. 2017, which claims the benefit of U.S. Provisional Application No. 62/366,682, filed on 26 Jul. 2016, each of which is hereby incorporated by reference.

TECHNICAL FIELD

The disclosure relates generally to plant growth and preservation, and more particularly, to treating mildew using ultraviolet and/or visible light.

BACKGROUND ART

The infection of green tissue, flower clusters and buds by spores results in fungal diseases common to the grape family and most agricultural crops. When spore infection occurs, conidia are produced and the disease spreads rapidly throughout the plant. The spread of disease is enhanced if the combination of temperature, leaf wetness and time are satisfied. Some of the fungal diseases that attack plants, such as grapes and strawberries in particular, are: (1) powdery mildew, (2) Downey mildew, (3) black rot, (4) Phomopsis Cane and Leaf Spot, (5) Eutypa Dieback.

To combat mildew, such as powdery mildew, a common approach is to apply liberal doses of fungicides by broad coverage spraying techniques using spray applicators. The use of chemical sprayers can produce potential side effects and/or be harmful to plants. The use of pesticides is compounded with problems for plant growers due to their chemical nature, the necessary safety precautions required, government regulations, and some consumers' reluctance to eat produce treated with pesticides. The spray operator, for his/her own safety, is required to wear protective clothing, a special breathing mask, eye goggles, and water proof gloves to prevent contamination by toxic pesticides.

Present fungicides work by being absorbed within the plant tissue (the fungicide is systemic) or providing a protective coating on the surface. The fungicide can act as a protectant to prevent infection, or if the plant is already infected, the fungicide can act as an eradicant to stop infection or as an antisporulant to prevent disease spread.

Ultraviolet radiation can be effective for combating various types of mildew. However, currently available mildew equipment generally employs ultraviolet mercury lamps radiating at a peak wavelength of 254 nanometers.

SUMMARY OF THE INVENTION

Aspects of the invention provide a solution for controlling mildew in a cultivated area. The solution can include a set of ultraviolet sources that are configured to emit ultraviolet and/or blue-ultraviolet radiation to harm mildew present on a plant or ground surface. A set of sensors can be utilized to acquire plant data for at least one plant surface of a plant, which can be processed to determine a presence of mildew on the at least one plant surface. Additional features can be included to further affect the growth environment for the plant. A feedback process can be implemented to improve one or more aspects of the growth environment.

A first aspect of the invention provides a system for controlling mildew, the system comprising: a set of ultraviolet sources, wherein the set of ultraviolet sources are configured to emit ultraviolet radiation, such as ultraviolet radiation in an ultraviolet range of approximately 260 nanometers to approximately 310 nanometers; a set of sensors for acquiring plant data for at least one plant surface of a plant; and a control system for selectively operating the set of ultraviolet sources to illuminate at least a portion of the plant in response to determining a presence of mildew on the at least one plant surface based on the plant data.

A second aspect of the invention provides a cultivated area comprising: a plurality of plants; and a system for controlling mildew on at least one of the plurality of plants, the system comprising: a set of ultraviolet light sources, wherein the set of ultraviolet light sources are configured to emit ultraviolet radiation, such as ultraviolet radiation in an ultraviolet range of approximately 260 nanometers to approximately 290 nanometers; a set of sensors for acquiring plant data for at least one plant surface of the at least one of the plurality of plants; and a control system for selectively operating the set of ultraviolet light sources to illuminate the at least one plant surface in response to determining a presence of mildew on the at least one plant surface based on the plant data.

A third aspect of the invention provides a system for controlling mildew, the system comprising: a control system for managing plant growth in a cultivated area, wherein the managing includes managing treatment of mildew when evaluated as being present on at least one plant in the cultivated area; and a plurality of movable plant treatment components, each plant treatment component including: a set of ultraviolet sources, wherein the set of ultraviolet sources are configured to emit ultraviolet radiation, such as ultraviolet radiation in an ultraviolet range of approximately 260 nanometers to approximately 310 nanometers; a set of sensors for acquiring plant data for at least one plant surface of a plant; and an onboard control device for controlling the set of ultraviolet light sources and the set of sensors and for communicating with the control system, wherein the onboard control device processes the plant data to determine a presence of mildew on the at least one plant, and the control system provides treatment instructions to the onboard control device for treating mildew determined to be present on the at least one plant using the set of ultraviolet sources.

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

FIGS. 8A and 8B show how attributes of ultraviolet radiation can be adjusted based on a plant, maturity of the plant, and/or purpose of the ultraviolet radiation, according to embodiments.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

As indicated above, aspects of the invention provide a solution for controlling mildew in a cultivated area. The solution can include a set of ultraviolet sources that are configured to emit ultraviolet and/or blue-ultraviolet radiation to harm mildew present on a plant or ground surface. A set of sensors can be utilized to acquire plant data for at least one plant surface of a plant, which can be processed to determine a presence of mildew on the at least one plant surface. Additional features can be included to further affect the growth environment for the plant. A feedback process can be implemented to improve one or more aspects of the growth environment. In an illustrative embodiment, a UV LED-based system with the feedback control is described to effectively combat mildew.

Ultraviolet radiation, which can be used interchangeably with ultraviolet light, means electromagnetic radiation having a wavelength ranging from approximately 10 nanometers (nm) to approximately 400 nm. Within this range, there is ultraviolet-A (UV-A) electromagnetic radiation having a wavelength ranging from approximately 315 nm to approximately 400 nm, ultraviolet-B (UV-B) electromagnetic radiation having a wavelength ranging from approximately 280 nm to approximately 315 nm, and ultraviolet-C (UV-C) electromagnetic radiation having a wavelength ranging from approximately 100 nm to approximately 280 nm. As used herein, blue-ultraviolet (blue-UV) radiation has a wavelength between approximately 380 nm to 420 nm.

As used herein, unless otherwise noted, the term "set" means one or more (i.e., at least one) and the phrase "any solution" means any now known or later developed solution. It is understood that, unless otherwise specified, each value is approximate and each range of values included herein is inclusive of the end values defining the range. As used herein, unless otherwise noted, the term "approximate" (and variations thereof) is inclusive of values within +/− ten percent of the stated value.

Figure 1:
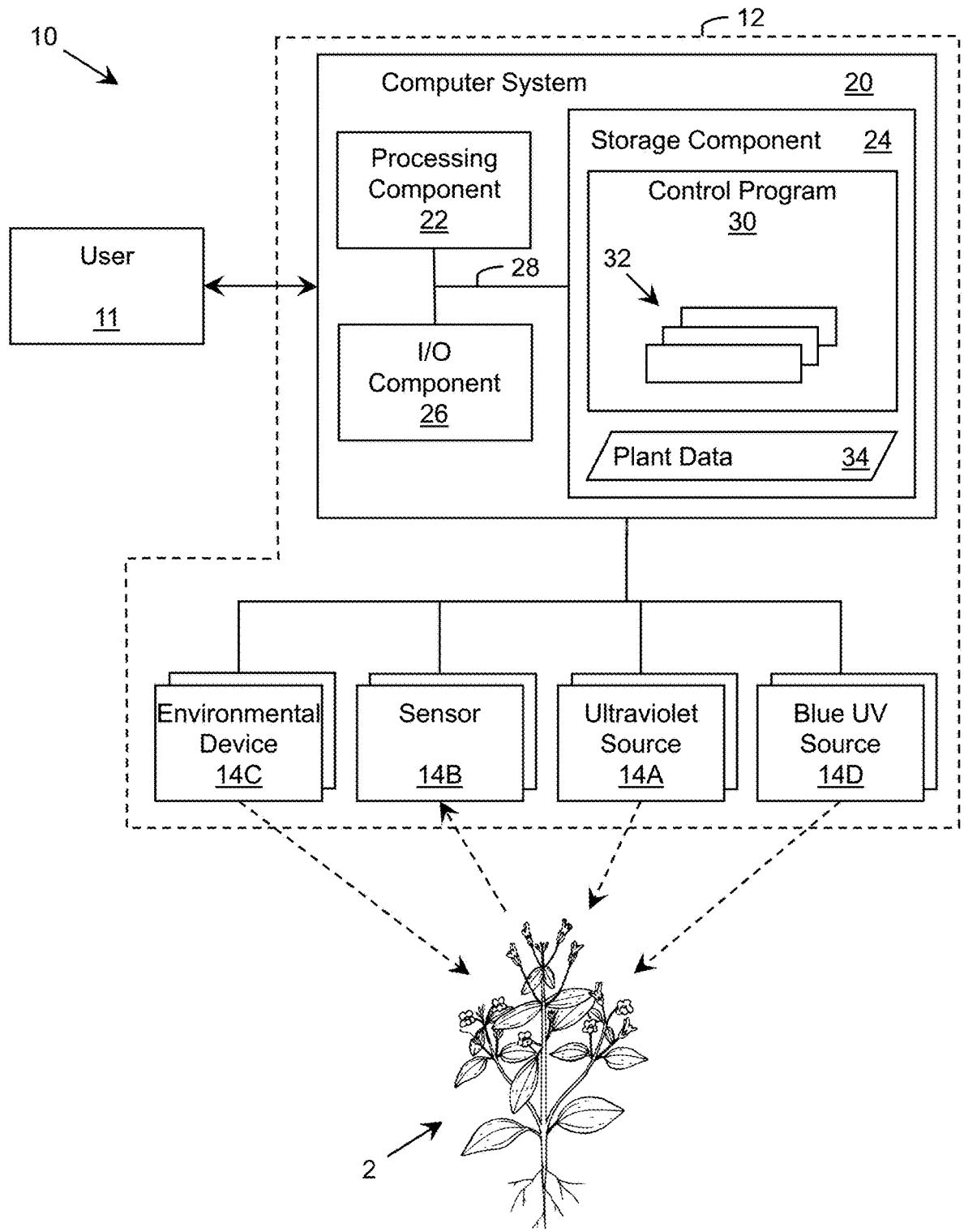
FIG. 1 shows an illustrative environment for controlling mildew on a plant according to an embodiment.

Turning to the drawings, FIG. 1 shows an illustrative environment 10 for controlling mildew on a plant 2 according to an embodiment. To this extent, the environment 10 includes a mildew control system 12 that can perform a process described herein in order to control mildew on the plant 2. In particular, the mildew control system 12 is shown including various I/O devices 14A-14D, each of which can acquire data regarding the plant 2 and/or a growth environment thereof and/or can affect one or more attributes of the plant 2 and/or the growth environment thereof. The mildew control system 12 can include a computer system 20, which includes a control program 30, which can cause the computer system 20 to operate the I/O devices 14A-14D and make the control system 12 operable to control mildew on the plant 2 by performing a process described herein.

The computer system 20 is shown including a processing component 22 (e.g., one or more processors), a storage component 24 (e.g., a storage hierarchy), an input/output (I/O) component 26 (e.g., one or more I/O interfaces and/or devices), and a communications pathway 28. In general, the processing component 22 executes program code, such as the control program 30, which is at least partially fixed in storage component 24. While executing program code, the processing component 22 can process data, such as plant data 34, which can result in reading and/or writing transformed data from/to the storage component 24 and/or the I/O component 26 for further processing. The pathway 28 provides a communications link between each of the components in the computer system 20.

The I/O component 26 can comprise one or more human I/O devices, which enable a human user 11 to interact with the computer system 20 and/or one or more communications devices to enable a system user 11 to communicate with the computer system 20 using any type of communications link. To this extent, the control program 30 can manage a set of interfaces (e.g., graphical user interface(s), application program interface, and/or the like) that enable human and/or system users 11 to interact with the control system 12. The I/O component 26 can further enable the computer system 20 to interact with each I/O device 14A-14D using any type of communications link. Such interactions can result in the acquisition of plant data 34, which can be processed by the computer system 20 to affect further operation of the I/O devices 14A-14D. Furthermore, the control program 30 can manage operation of the I/O devices 14A-14D and manage (e.g., store, retrieve, create, manipulate, organize, present, etc.) the data, such as plant data 34, using any solution.

In any event, the computer system 20 can comprise one or more general purpose computing articles of manufacture (e.g., computing devices) capable of executing program code, such as the control program 30, installed thereon. As used herein, it is understood that "program code" means any collection of instructions, in any language, code or notation, that cause a computing device having an information processing capability to perform a particular action either directly or after any combination of the following: (a) conversion to another language, code or notation; (b) reproduction in a different material form; and/or (c) decompression. To this extent, the control program 30 can be embodied as any combination of system software and/or application software.

Furthermore, the control program 30 can be implemented using a set of modules 32. In this case, a module 32 can enable the computer system 20 to perform a set of tasks used by the control program 30, and can be separately developed and/or implemented apart from other portions of the control program 30. As used herein, the term "component" means any configuration of hardware, with or without software, which implements the functionality described in conjunction therewith using any solution, while the term "module" means program code that enables a computer system 20 to implement the actions described in conjunction therewith using any solution. When fixed in a storage component 24 of a computer system 20 that includes a processing component 22, a module is a substantial portion of a component that implements the actions. Regardless, it is understood that two or more components, modules, and/or systems may share some/all of their respective hardware and/or software. Furthermore, it is understood that some of the functionality discussed herein may not be implemented or additional functionality may be included as part of the computer system 20.

When the computer system 20 comprises multiple computing devices, each computing device can have only a portion of the control program 30 fixed thereon (e.g., one or more modules 32). However, it is understood that the computer system 20 and the control program 30 are only representative of various possible equivalent computer systems that may perform a process described herein. To this extent, in other embodiments, the functionality provided by the computer system 20 and the control program 30 can be at least partially implemented by one or more computing devices that include any combination of general and/or specific purpose hardware with or without program code. In each embodiment, the hardware and program code, if included, can be created using standard engineering and programming techniques, respectively.

Regardless, when the computer system 20 includes multiple computing devices, the computing devices can communicate over any type of communications link. Furthermore, while performing a process described herein, the computer system 20 can communicate with one or more other computer systems using any type of communications link. In either case, the communications link can comprise any combination of various types of optical fiber, wired, and/or wireless links; comprise any combination of one or more types of networks; and/or utilize any combination of various types of transmission techniques and protocols. Illustrative wireless communications technologies include Wi-Fi and Bluetooth. Regardless, the communications link can enable the user 11 to be located remote from the computer system 20. For example, a user 11 can comprise a remote computer used to transmit operational instructions to the computer system 20 (e.g., using a wireless communications link). The operational instructions can be used to program functions performed and managed by the computer system 20. Similarly, the computer system 20 can transmit data calculations (e.g., changes), data from the sensors, etc., to the user 11 (e.g., the remote computer), to facilitate further use of the control system with treating the surface 4.

As discussed herein, the control system 12 can be configured to control mildew on the plant 2, such as the plant leaves, using any of various possible combinations of I/O devices 14A-14D. As illustrated, the control system 12 can include a set of ultraviolet sources 14A. Furthermore, an embodiment of the control system 12 can include a set of blue-ultraviolet (blue-UV) sources 14D. Each set of ultraviolet sources 14A, 14D can include any combination of one or more types of devices configured to emit ultraviolet or blue-UV radiation during the operation thereof. Illustrative types of ultraviolet or blue-UV sources 14A, 14D include: an ultraviolet or blue-UV light emitting diode (LED); a high intensity ultraviolet lamp (e.g., high intensity mercury lamp); a discharge lamp; a super luminescent LED; a laser diode; and/or the like. An ultraviolet or blue-UV source 14A, 14D can be configured to emit a broad spectrum of ultraviolet radiation (e.g., spectral distribution with multiple peak wavelengths or a peak over a range of wavelengths) or a narrow spectrum of ultraviolet or blue-UV radiation (e.g., spectral distribution with a single sharp peak wavelength).

In an embodiment, an ultraviolet or blue-UV source 14A, 14D can include a set of LEDs manufactured with one or more layers of materials selected from the group-III nitride material system (e.g., $Al_xIn_yGa_{1-x-y}N$, where 0≤x, y 1, and x+y≤1 and/or alloys thereof). Additionally, an ultraviolet or blue-UV source 14A, 14D can comprise one or more additional components (e.g., a wave guiding structure, a component for relocating and/or redirecting emitter(s), etc.) to direct and/or deliver the emitted radiation to a particular location/area, in a particular direction, in a particular pattern, and/or the like. Illustrative wave guiding structures can include, but are not limited to, a wave guide, a plurality of ultraviolet fibers, each of which terminates at an opening, a diffuser, and/or the like.

Additionally, the control system 12 can include a set of sensors 14B. Each sensor 14B can be configured to acquire data regarding any combination of one or more of various attributes of the plant 2 and/or its growth environment. Illustrative sensors 14B include: radiation (visible light (optical), ultraviolet, infrared, microwave, terahertz, and/or the like) sensors; humidity sensors; temperature sensors; gas (e.g., carbon dioxide) sensors; etc. In an embodiment, the set of sensors 14B includes at least one sensor capable of acquiring data regarding the plant 2 that enables the control system 12 to detect mildew and/or bacteria. Additionally, the set of sensors 14B can include one or more sensors for acquiring data regarding the plant 2 that enables the control system 12 to determine an overall health of the plant 2.

The control system 12 also can include a set of environmental devices 14C, which can be operated to affect one or more attributes of the growth environment of the plant 2. Illustrative environmental devices 14C include: a water source; a chemical treatment (e.g., pesticide, fungicide, and/or the like) source; a gas (e.g., carbon dioxide) source; an air source; a water vapor source; a heating and/or cooling device; a light (e.g., visible, ultraviolet, infrared, and/or the like) source; a humidifier; a dehumidifier; etc. Illustrative light sources include visible light emitting diodes, incandescent light, infrared light emitting diodes, ultraviolet lamps, etc. In an illustrative embodiment, the air source can comprise a fan or the like, which can generate a wind to cause movement of one or more surfaces of the plant, thereby enabling ultraviolet, chemical, and/or other treatment on various surfaces.

Additional aspects of the invention are shown and described in conjunction with particular combinations of some or all of the types of I/O devices 14A-14D. It is understood that the invention is not limited to the embodiments of the particular combinations shown in the drawings. Additionally, it is understood that a drawing may not show all components of a control system 12 for clarity of illustration of the unique features being illustrated. To this extent, unless explicitly stated otherwise, each of the additional embodiments shown and described herein can be implemented in combination with one or more features shown and described in conjunction with other embodiments. However, it is understood that various embodiments can be implemented without all of the features shown and described herein.

It is understood that the computer system 20 can adjust the various operating parameters of the I/O devices 14A-14D based on plant data and/or a pre-determined treatment schedule. A treatment schedule can be configured for a particular type of plant 2, type and/or location of a surface of the plant being treated, a maturity of the plant 2 (e.g., where in the growth cycle), and/or one or more attributes of the growth environment for the plant 2. For example, the computer system 20 can adjust a set of attributes for ultraviolet treatment of a plant 2 based on whether the plant is in a blooming stage, fruit formation stage, seedling stage, pre-harvest stage, and/or the like. In an embodiment, the control system can selectively move some or all of the I/O devices 14A-14D to evaluate and/or treat a plant 2. Such movement can enable a set of I/O devices 14A-14D to evaluate and/or treat different surfaces of a plant 2, multiple plants within a cultivated area, and/or the like.

In an embodiment, the computer system 20 can allow the user 11 to adjust at least one of a plurality of operating parameters. This can include making adjustments during the operation of one or more of the radiation sources 14A, 14C, 14D and/or prior to initiating a treatment of a plant 2. In one embodiment, the I/O component 26 can include a set of buttons and/or a touch screen to enable a human user 11 to specify various input selections regarding the operating parameters. In one embodiment, the I/O component 26 can include a visual display for providing status information on the irradiation of the plant 2 (e.g., time remaining, humidity, presence of water, or the like), status information of a surface of the plant, a visual indicator that displays whether irradiation is underway (e.g., an illuminated light), or if the irradiation is over (e.g., absence of an illuminated light), etc.

An embodiment of the control system 12 described herein can be implemented at a cultivated area including numerous plants, such as a farm field, a greenhouse, and/or the like. The plants can be of the same type or numerous types, and can be of the same or varying maturities. To this extent, the control system 12, or components thereof, can be selectively moved to evaluate and/or treat plants 2 located in different regions of the cultivated area. Additionally, an embodiment of the control system 12 can include multiple plant treatment components, which are managed by one or more central control components. In this case, each plant treatment component can include a set of I/O devices 14A-14D and an onboard control device (e.g., a computer system) for operating the set of I/O devices 14A-14D. The onboard control device can communicate with the central control component to send and receive information. For example, the onboard control device can provide the central control component with information regarding the plant(s) and the presence of mildew or bacteria, while the central control component can provide the onboard control device with information regarding a region to evaluate and/or treat, a treatment program, and/or the like.

An embodiment of the control system 12 can include numerous physically distinct components. The physically distinct components can include multiple types of components, each type of component having a unique purpose. Additionally, one or more of the physically distinct components can operate autonomously or the operation can be controlled by a central control component. For example, such physically distinct components can include components for evaluating and/or treating a plant for the presence of mildew, components for affecting a growth environment of a plant, components for harvesting fruit or vegetables from a plant, and/or the like.

Figure 2A:
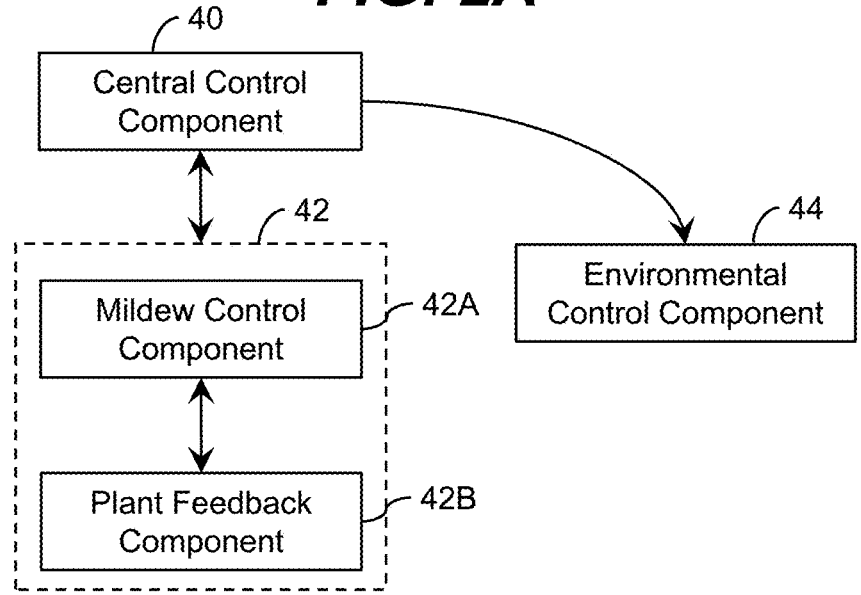
FIGS. 2A and 2B show component views of more particular illustrative control systems according to embodiments.
Figure 2B:
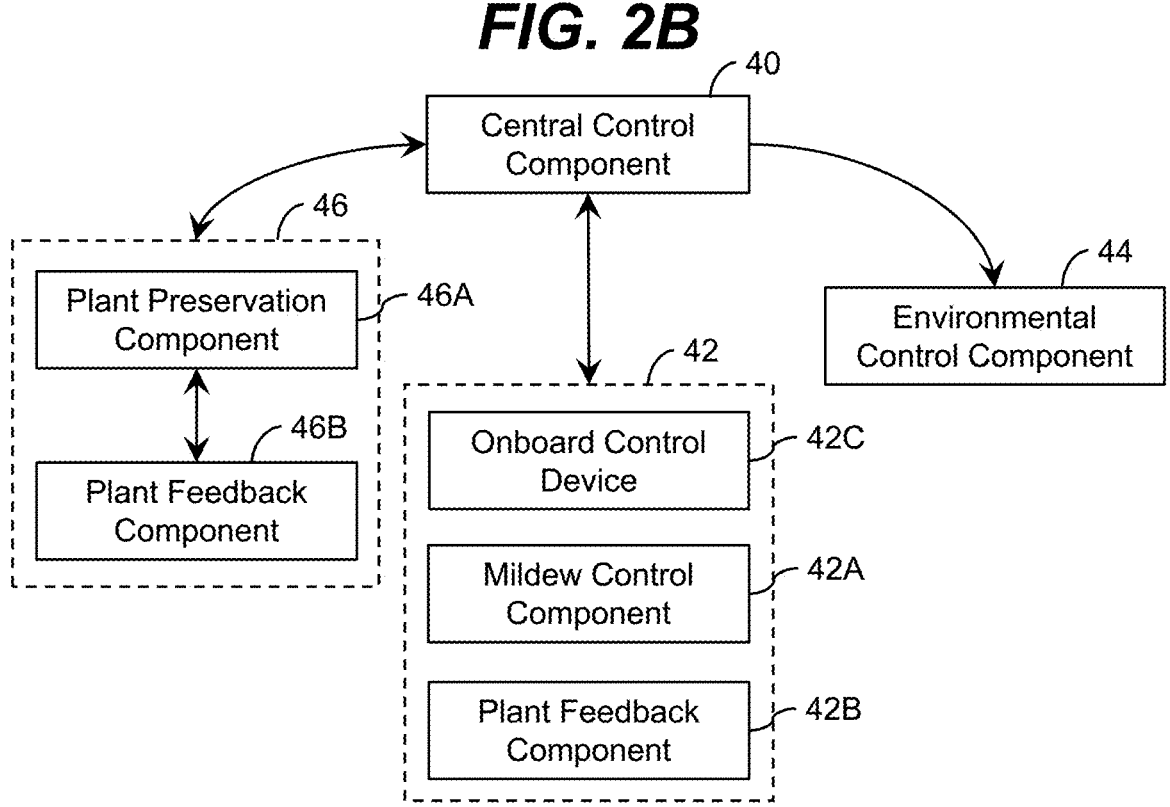

To this extent, FIGS. 2A and 2B show component views of more particular illustrative control systems according to embodiments. In FIG. 2A, the control system includes a central control component 40 which can comprise a computer system located at a fixed location. The central control component 40 can communicate with (e.g., using a wireless communications solution) and control one or more plant treatment components 42. Each plant treatment component 42 can include a mildew control component 42A, which includes one or more I/O devices for treating mildew (e.g., ultraviolet sources, fungicide source, and/or the like). Additionally, a plant treatment component 42 can include a plant feedback component 42B, which can include one or more devices (e.g., radiation sensor) to acquire feedback data regarding the plant. For example, the feedback data can be processed by an onboard control device 42C (FIG. 2B, e.g., a computer system) located on the plant treatment component 42 to identify area(s) of the plant requiring treatment, determine an effectiveness of treatment, identify a type of problem (e.g., type of mildew, bacteria, and/or the like) requiring treatment, etc. The plant treatment component 42 (e.g., the onboard control device 42C) can provide feedback to the central control component 40 after the plant has been evaluated and/or treated.

Additionally, the central control component 40 is shown communicating with an environmental control component 44. To this extent, the central control component 40 can operate various devices included in the environmental control component 40 to affect one or more attributes of a growth environment for the plants. For example, the central control component 40 can operate a water source, an artificial lighting source, and/or the like, which can make the growth environment more conducive for healthy growth of the plant. In an embodiment, the environmental control component 44 can include various devices, which may be located at fixed locations or moved to different locations by the central control component 40. Regardless, the central control component 40 can coordinate operation of the environmental control component 44 with the plant treatment component 42 to ensure that the operation of one component does not adversely interfere with the operation of another component. For example, the central control component 40 can ensure that a scheduled watering does not occur prior to or during treatment being performed by the plant treatment component 42.

The control system shown in FIG. 2B is further shown including a plant growth component 46, which can include a set of I/O devices configured to evaluate and/or assist the plant in growing healthy, e.g., in response to a parasitic attack (e.g., mildew) and the subsequent treatment by the plant treatment component 42. For example, the plant growth component 46 can include a plant preservation component 46A, which includes a set of I/O devices for promoting plant photosynthesis, increase of flavonoids, and/or the like. To this extent, the plant preservation component 46A can include ultraviolet source(s), which can emit ultraviolet radiation in a range of 280 nm to 300 nm (285-295 nm in a more particular embodiment), visible light source(s), and/or the like. The plant feedback component 46B can include a set of I/O devices, which can acquire plant data that enables the plant growth component 46 (e.g., an onboard control device) to determine what assistance the plant requires, if any, as well as an effectiveness of the assistance. The plant growth component 46 (e.g., the onboard control device) can provide data regarding the health of the plant, any assistance provided, and/or an effectiveness of such assistance for processing by the central control component.

An embodiment of the central control component 40 can use data provided by the plant treatment component 42 and/or the plant growth component 46 to evaluate and adjust one or more aspects of the operation of the various components 42, 44, 46 as part of a feedback loop in order to determine a set of target parameters for treating and/or assisting plant growth. To this extent, FIG. 3 shows an illustrative feedback process, which can be implemented by a control system described herein, according to an embodiment.

Figure 3:
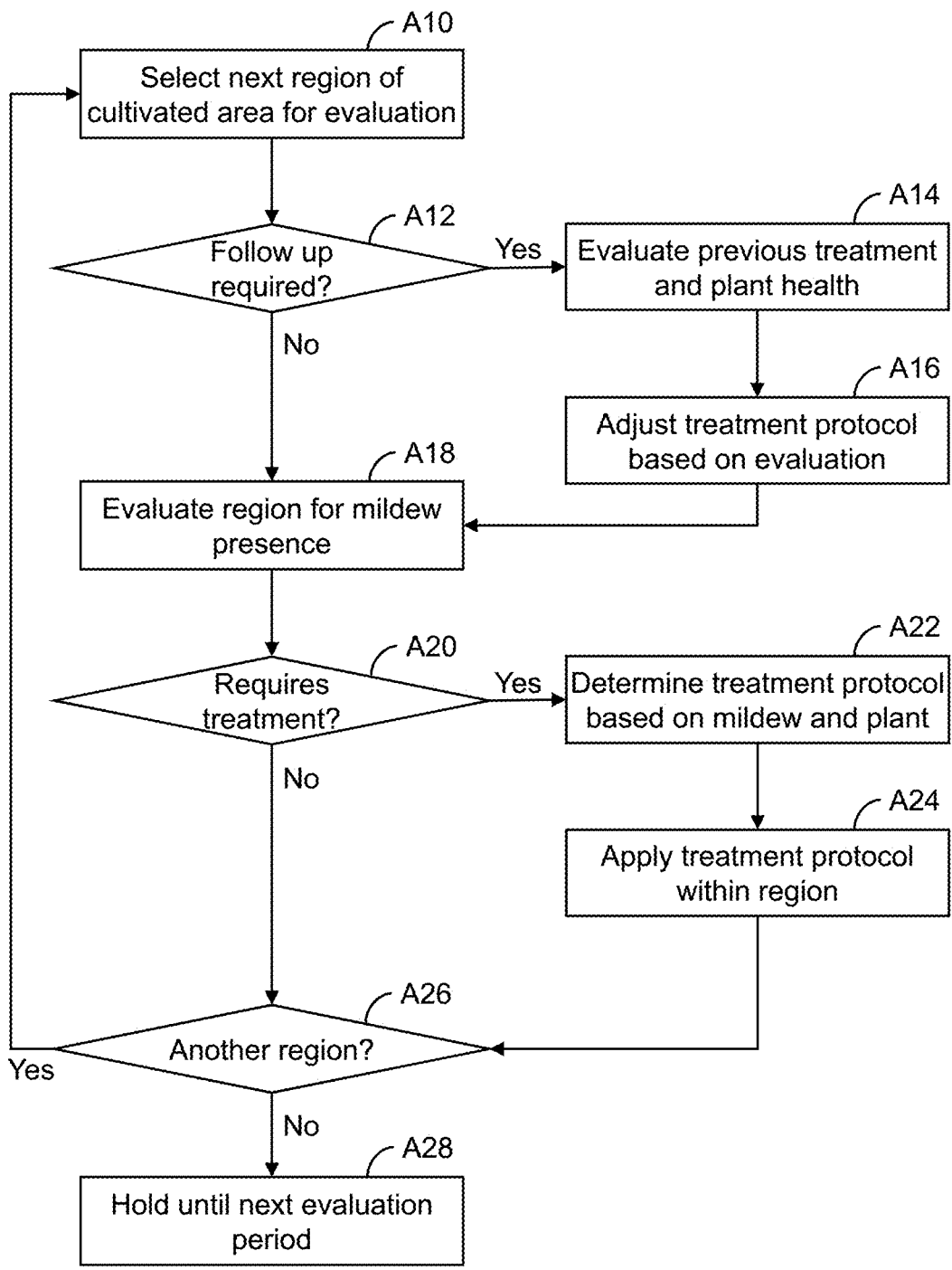
FIG. 3 shows an illustrative feedback process, which can be implemented by a control system described herein, according to an embodiment.

Referring to FIGS. 2B and 3, in action A10, the central control component 40 can select a next region of a cultivated area for evaluation, e.g., by one of a set of plant treatment components 42. The central control component 40 can provide instructions for the plant treatment component 42 to move to the selected region and evaluate the plant(s) located at the region. In an embodiment, a control system can include multiple plant treatment components 42 operated by the central control component 40. In this case, the central control component 40 can direct multiple plant treatment components 42 to different regions of the cultivated area to perform the process described herein in parallel for the different regions.

The evaluation can be a follow up evaluation after a previous treatment for mildew or a periodic evaluation to determine whether any mildew or other parasitic attack is present on the plant(s). To this extent, in action A12, the central control component 40 can determine whether the region has been previously treated for a parasitic attack, and if so, whether a follow up evaluation is required.

When a follow up evaluation is required, in action A14, the plant treatment component 42 can evaluate an effectiveness of the previous treatment as well as a current state of the plant health. For example, the plant treatment component 42 can obtain image data on the plant, particularly any surfaces of the plant treated for the mildew, and process the image data to determine whether any mildew remains after the treatment and/or a health of the treated region and/or the plant as a whole.

In action A16, the central control component 40 can make one or more adjustments to a treatment protocol, if necessary, based on the feedback acquired by the plant treatment component 42. For example, the central control component 40 can adjust one or more attributes of the ultraviolet radiation used during the treatment protocol, supplement the ultraviolet radiation with an additional treatment, and/or the like. Such adjustments can include one or more of: the time, intensity, and/or spectral power distribution, of the radiation used, in order to target the parasitic attack without significantly affecting (negatively) the plant. Additionally, the adjustments can include adjustments to a position (vertical and/or horizontal) of the I/O devices with respect to the plant. The central control component 40 can individualize one or more adjustments based on the species of the plant, a maturity of the plant, a type of parasitic attack, a location of the plant within the cultivated area, and/or the like. Regardless, the central control component 40 can store the revised treatment protocol for use in future treatment(s) of plant(s) in the cultivated area.

In an embodiment, adjustments to a treatment protocol can be made by a user 11 (FIG. 1). For example, the central control component 40 can generate a map of the cultivated area that indicates various region(s) in which mildew growth has been identified and treated. Additionally, the map can indicate an effectiveness of the treatment performed. The central control component 40 can provide the map for presentation to the user 11. The user 11 can review the map and provide feedback to the central control component 40. Such feedback can identify one or more changes to the treatment protocol to be made by the central control component 40. Illustrative changes include changes to the intensity, duration, and/or spectral power distribution of the ultraviolet radiation, a location of the ultraviolet sources, and/or the like. In a more particular embodiment, the user 11 comprises an individual utilizing a smart phone app to review the map and identify change(s) to the treatment protocol.

Regardless, in action A18, the plant treatment component 42 can evaluate plant(s) within the region for the presence of one or more parasites, such as mildew. In action A20, the plant treatment component 42 can determine whether a plant requires treatment. If so, in action A22, the plant treatment component 42 can obtain a treatment protocol from the central control component 40. For example, the treatment protocol can be customized according to an extent of the parasitic attack, a type of the plant, a maturity of the plant, an effectiveness of a previous treatment, and/or the like. In action A24, the plant treatment component 42 can apply the treatment protocol to the plant(s) within the region.

Once complete, in action A26, the plant treatment component 42 can determine whether another region requires evaluation. If so, the process can return to action A10, and the plant treatment component 42 can receive instructions from the central control component 40. When no other region requires evaluation, in action A28, the plant treatment component 42 can hold until the next evaluation period arrives. For example, the plant treatment component 42 can move to a location away from the plants within the cultivated area and enter a low power (sleep) mode until receiving a signal from the central control component 40.

When an entire cultivated area has been evaluated and/or treated, the central control component 40 can determine when subsequent evaluation and/or treatment may be required. For example, the central control component 40 can record the region(s), if any, in which mildew treatment was performed and flag such regions and any surrounding regions for follow up at an earlier time than any regions in which the evaluation indicated no mildew was present. Such follow up can evaluate the effectiveness of the treatment as well as determine whether the mildew has spread to any of the surrounding regions.

While the process of FIG. 3 illustrates a feedback process for refining and improving the treatment of mildew, it is understood that a control system described herein can use a similar process to refine and improve operation of the plant growth component 46. Additionally, feedback acquired by the plant treatment component 42 and/or the plant growth component 46 can be used by the central control component 40 to adjust and refine one or more aspects of operating any other components, such as the environmental control component 44 and/or the other of the plant treatment component 42 and/or the plant growth component 46. For example, the central control component 40 can adjust one or more of: an amount and/or type of visible radiation (e.g., wavelengths centered at 430 nm and 650 nm); an amount of infrared radiation; and/or the like. Other illustrative growth conditions for a plant that can be adjusted by the central control component 40 include: humidity level; temperature; water levels within the soil; nutrient content; water pH balance; ethylene levels; carbon dioxide levels; vapor levels; etc. Additionally, the central control component 40 can record and evaluate other attributes of the growth environment and their affect on the growth of the plant, such as a density of the plantings, a location within the cultivated area, and/or the like.

As discussed herein, a control system described herein can include any combination of various I/O devices utilized in the evaluation and/or treatment of plant(s). Additionally, these I/O devices can include I/O devices that are movable with respect to the plant(s) and/or I/O devices that are located in a fixed position. A particular solution for locating and/or moving the I/O devices as well as a particular combination of I/O devices can be selected based on the type(s) of evaluation and/or treatment/growth assistance to be performed as well as one or more attributes of the plant and the corresponding growth environment.

Figure 4A:
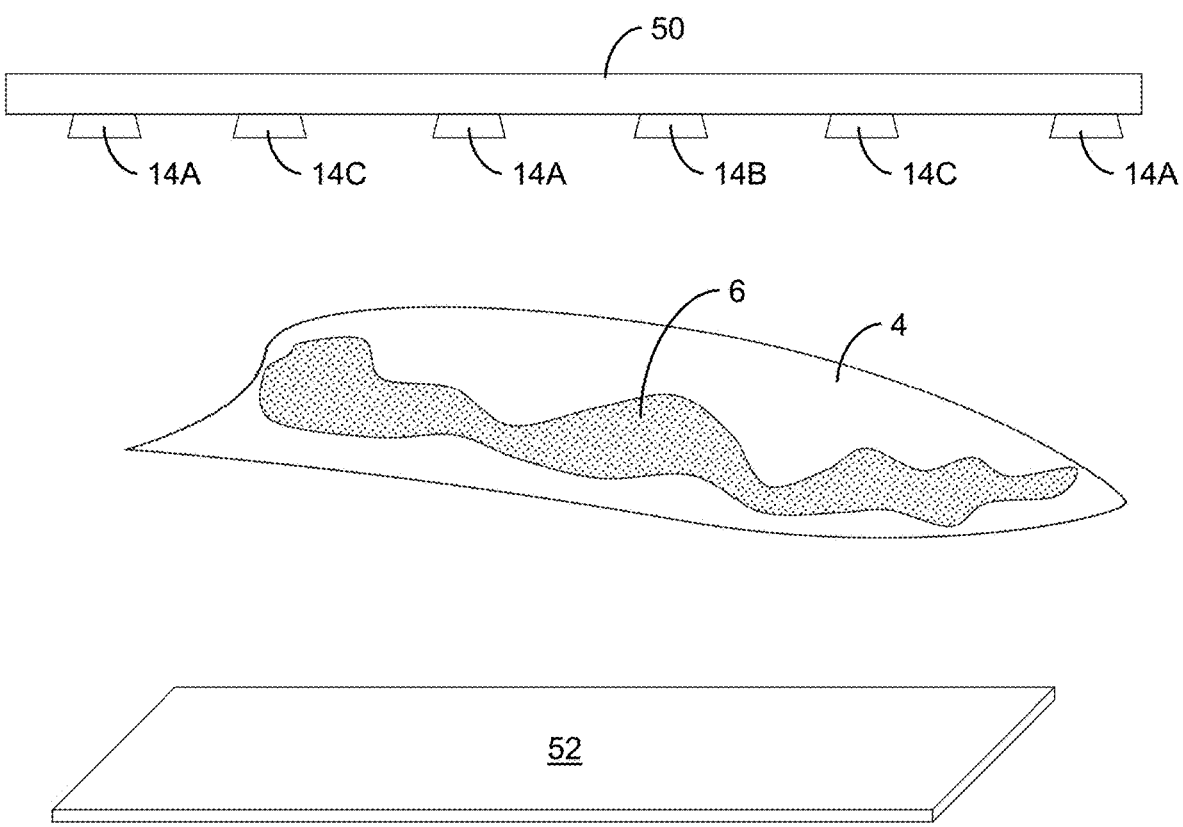
FIG. 4A-4C show more specific illustrative configurations of I/O devices of a control system according to embodiments.
Figure 4B:
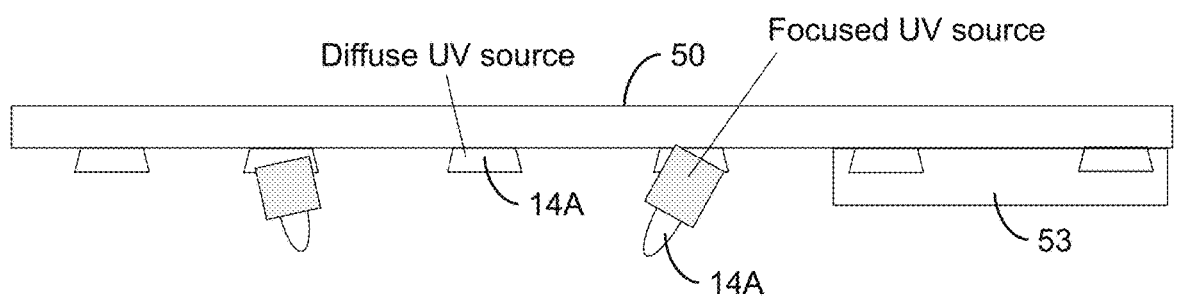
Figure 4C:
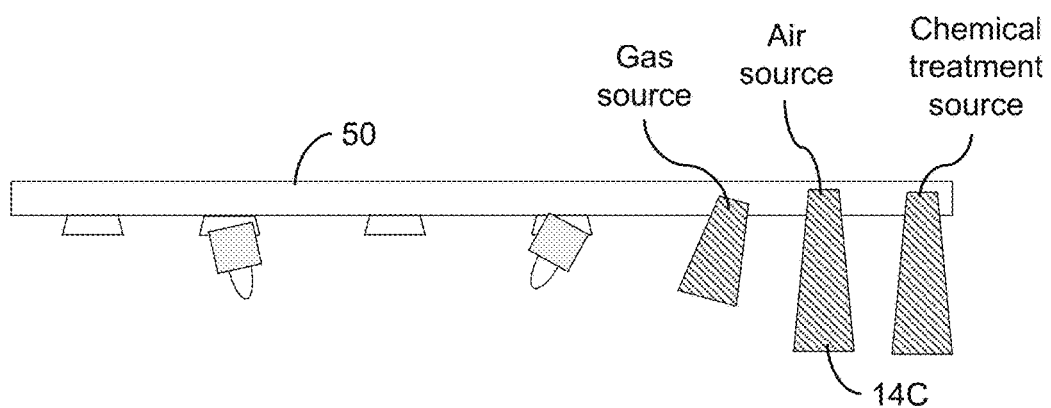

FIGS. 4A-4C show more specific illustrative configurations of I/O devices 14A-14C of a control system 12 (FIG. 1) according to embodiments. As illustrated in FIG. 4A, the control system includes a support structure 50, which supports a set of I/O devices 14A-14C oriented with respect to a surface 4 of a plant 2 (FIG. 1) to enable evaluation and treatment of the plant surface 4 by the control system using the set of I/O devices 14A-14C. For example, the I/O devices 14A-14C can acquire data used to detect the presence of mildew 6 and irradiate the plant surface 4 with ultraviolet radiation to treat the mildew 6, which may be present thereon.

In a more particular illustrative embodiment, the support structure 50 can include multiple ultraviolet sources 14A, which can be operated to deliver ultraviolet radiation having a predetermined target intensity distribution to match coverage of the mildew 6 on the plant surface 4. The ultraviolet sources 14A can be configured to emit ultraviolet radiation having a peak wavelength in a range of 260 nanometers to 310 nanometers (260 to 290 nanometers in a more particular embodiment and 270 to 290 nanometers in an even more particular embodiment). The ultraviolet sources 14A can include wavelength subsets of ultraviolet sources, where each wavelength subset includes one or more ultraviolet sources configured to emit ultraviolet radiation having a peak wavelength different from the peak wavelength emitted by the ultraviolet source(s) in the other wavelength subset(s). Additionally, the ultraviolet sources 14A can include area subsets of ultraviolet sources, each of which corresponds to a different physical area of illumination. In this case, each area subset can include multiple wavelength subsets.

The control system can operate the ultraviolet sources 14A as a group, in individual subsets, and/or each ultraviolet source 14A individually, in order to provide a desired irradiation of the plant surface 4. To this extent, based on feedback data acquired by the set of sensors 14B, the control system can adjust at least one attribute of the ultraviolet radiation generated by the ultraviolet source(s) 14A to effectively sterilize mildew or bacteria present on the plant surface 4. For example, the control system can adjust one or more of: a radiation intensity; a dose; a duration; a spectral power distribution; a direction; a location on the plant surface 4; a polarization; and/or the like. The control system can implement such adjustments by altering a particular combination of ultraviolet source(s) being operated, operating ultraviolet source(s) in pulsed or continuous mode, and/or the like.

Additionally, the support structure 50 can include one or more sensors 14B for acquiring data to detect the mildew 6. For example, in an illustrative embodiment, the support structure 50 can include at least one visible camera 14B, which can acquire image data of the plant surface 4. However, it is understood that a visible camera is only illustrative of various sensors that can be implemented to acquire data capable of being processed to determine the presence of mildew and/or bacteria on the plant surface 4. Other illustrative sensors 14B include: infrared, terahertz, ultraviolet, and microwave detectors, each of which can acquire data for determining the presence of bacteria or mildew on the plant surface 4.

Regardless, a sensor 14B can acquire data corresponding to reflectivity measurements from the plant surface 4, which the control system can analyze to identify differences between the reflectivity of mildew or bacteria versus that for a plant surface 4 without the presence of any significant amount of mildew or bacteria. Similarly, a sensor can acquire data regarding a fluorescent signal from the plant surface 4, which the control system can analyze for the presence of mildew or bacteria. For example, for an image-based sensor 14B, the control system (e.g., the computer system 20 of FIG. 1) can process the image data to determine the presence and extent of the mildew 6. Additionally, the plant data can be processed to determine a density of the mildew 6 on the plant surface 4, e.g., by evaluating one or more attributes of the mildew 6 in the image data (e.g., color) and/or fluorescent signal (e.g., strength of fluorescence). The control system can adjust an intensity of the ultraviolet radiation emitted by the ultraviolet sources 14A based on the density of the mildew 6.

The control system also can evaluate data acquired by the sensor(s) 14B to determine an effect of a previous treatment performed on the plant surface 4. For example, the plant data can be evaluated to determine whether any mildew remains after the treatment, an affect of the ultraviolet radiation on the plant (e.g., changes in the plant due to the ultraviolet irradiation), and/or the like. The control system can adjust one or more attributes of a future treatment based on the evaluation.

To facilitate the acquisition of plant data of sufficient quality for evaluation by the control system, the support structure 50 also can include a set of environmental devices 14C, which can be operated in conjunction with one or more of the sensor(s) 14B. For example, when the sensor 14B is an imaging device, such as a visible camera, the environmental devices 14C can include one or more sources of the radiation being imaged, such as a visible light sources, which can be operated in conjunction therewith. Similarly, to evaluate fluorescence, the environmental devices 14C can include a source of radiation that induces the fluorescence, which can be operated in conjunction with the sensor(s) 14B.

The control system 12 can adjust and distribute the intensity of the radiation over the plant surface 4 to effectively combat mildew 6 at a location determined to have a presence of the mildew by processing plant data as described herein. In addition to adjusting operation of the ultraviolet sources 14A, the control system can physically move the ultraviolet sources 14A to direct ultraviolet radiation at a target location. To this extent, the support structure 50 can be connected to any type of mechanism that allows movement of the I/O devices mounted thereto in any combination of two or more directions with respect to the plant surface 4. For example, the support structure 50 can have a range of motion in the vertical direction and/or horizontal direction, as well as a being rotatable about an axis and/or rotatable about an end over a range of degrees. The control system can utilize such movement to appropriately place the I/O devices for the evaluation and/or treatment of the plant surface 4.

In an embodiment, a control system described herein can utilize one or more additional components for directing ultraviolet radiation to a desired location. For example, a control system can utilize an ultraviolet mirror 52, which can redirect ultraviolet radiation emitted by the ultraviolet source(s) 14A to a surface of the plant, such as an underside of a leaf. Similar to the support structure 50, the ultraviolet mirror 52 can be relocatable with respect to the plant(s). Alternatively, the ultraviolet mirror 52 can be placed within the plant growth environment, e.g., over the soil. The ultraviolet mirror 52 can be formed of any type of ultraviolet reflective material including, for example, polished aluminum, polymer films, such as a fluoropolymers (e.g., PTFE, EFEP, ETFE, etc.), and/or the like.

A set of I/O devices also can include ultraviolet and/or other radiation sources that emit radiation having differing irradiation polar distributions. For example, as illustrated in FIG. 4B, a support structure 50 can include ultraviolet source(s) that emit diffuse radiation, and ultraviolet source(s) that emit focused radiation. As used herein, it is understood that a focused radiation source is a source that delivers at least 10% of the radiated intensity in a surface area being at most 10 times a diameter of the radiation source located at least 10 cm from the emitting surface of the radiation source. A diffuse radiation source is any source that does not meet the criteria of a focused radiation source. In an embodiment, a diffusiveness of radiation emitted by a set of radiation sources can be increased using one or more diffusive transparent elements 53, such as a solution described in U.S. patent application Ser. No. 14/478,266, which is hereby incorporated by reference. In an embodiment, one or more of the radiation sources 14A can be mounted to the support structure 50 in a manner that allows the radiation source 14A to be moved (e.g., rotated) with respect to the support structure 50.

It is understood that a particular support structure 50 can include any combination of ultraviolet sources, sensors, and/or environmental devices. To this extent, FIG. 4C shows an illustrative support structure 40 including ultraviolet sources and a combination of various environmental devices 14C. In this case, the environmental devices include a gas source, an air source, and a chemical treatment source. However, it is understood that this particular combination is only illustrative of various possible combinations. Additionally, it is understood that the arrangements shown in FIGS. 4A-4C are only illustrative schematic representations and embodiments of the invention are not limited to the arrangements shown.

Figure 5:
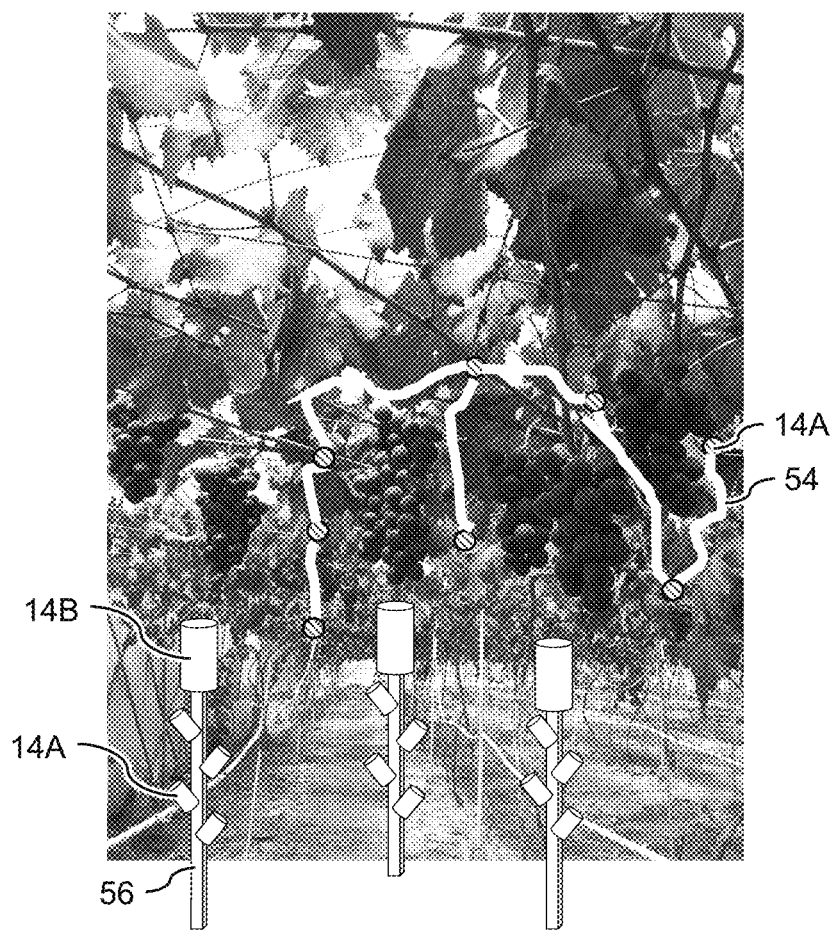
FIG. 5 shows a more specific illustrative configuration of I/O devices of a control system according to an embodiment.

Embodiments of a control system described herein can use any of various approaches for locating ultraviolet sources and/or other I/O devices with respect to a plant. For example, FIG. 5 shows a more specific illustrative configuration of I/O devices of a control system according to an embodiment. In this case, the plants are grape plants, which are suspended from a structure. As illustrated, a mesh 54 can be utilized to position one or more I/O devices (e.g., ultraviolet sources 14A) in a canopy of the plant, e.g., adjacent to the grapes hanging from the structure. It is understood that this is only an illustrative use of the mesh, which could be utilized to locate any of various I/O devices in any of various locations, such as on the ground and/or near roots and the soil of plants, to prevent mildew from growing thereon. Additionally, the mesh 54 can be located near the bottom of the plant to irradiate the bottom of the plant leaves, the lower leaves, the trunk of the plant, and/or the like. The mesh 54 can be any type of mesh, such as a mesh/net typically used for Christmas lights. To this extent, the mesh 54 can include ultraviolet sources 14A arranged in a two-dimensional pattern with the spacing selected based on the corresponding application.

Additionally, the control system can include one or more poles 56, each of which can support one or more I/O devices 14A, 14B therefrom. For example, a pole 56 can include one or more ultraviolet sources 14A and/or one or more sensors 14B, such as an imaging device described herein. The poles 56 can have a fixed height or be retractable. In the latter case, the poles 56 can extend to locate the I/O devices 14A, 14B in a manner that follows the growth of the plants. Additionally, the poles 56 can retract between uses of the I/O devices 14A, 14B to avoid interfering with other operations in the cultivated area.

Figure 6A:
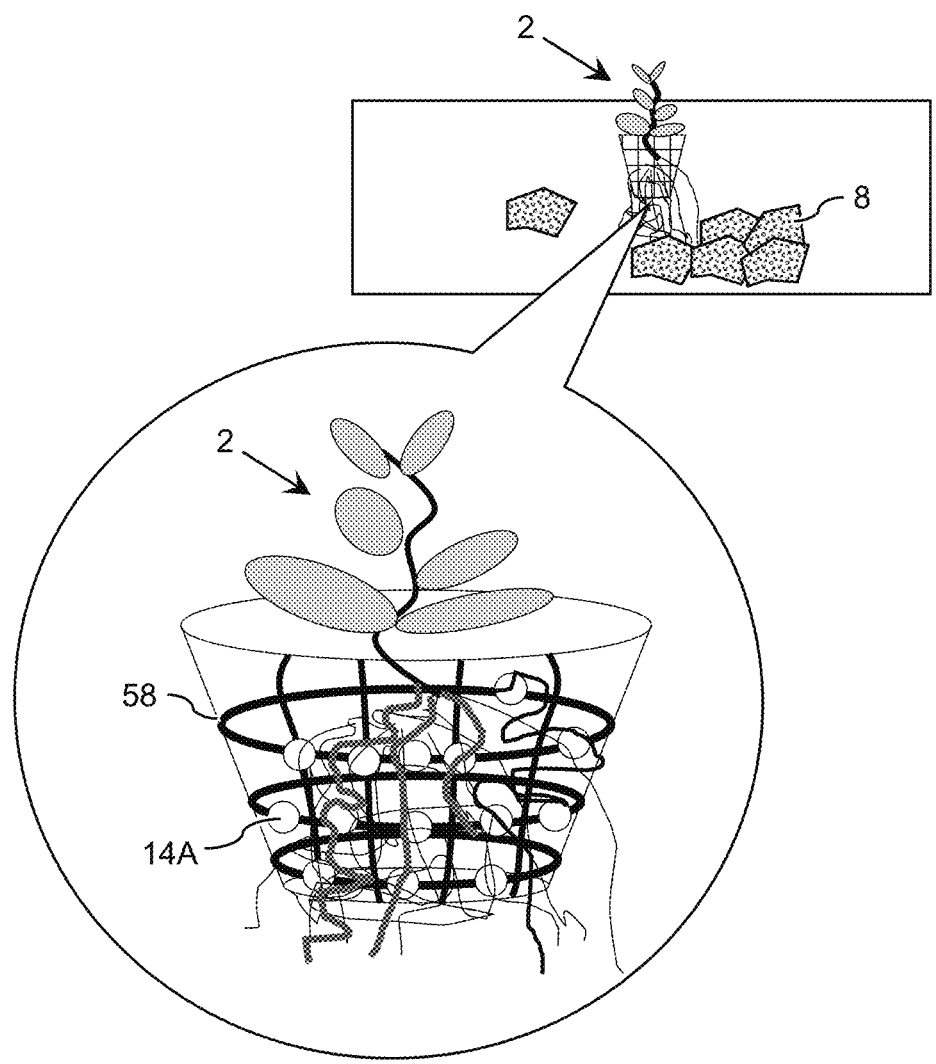
FIGS. 6A and 6B show illustrative configurations of I/O devices of a control system for treating roots of a plant according to an embodiment.

FIG. 6A shows an illustrative configuration of I/O devices of a control system for treating roots of a plant according to an embodiment. Such a configuration can be utilized, for example, in plants grown hydroponically, without the presence of soil. In this case and/or for other types of plants, at least some of the root structure of the plant 2 can be exposed to air outside of any type of ground or mix 8. Regardless, the root treatment system can include ultraviolet sources 14A located on a mesh-like structure 58 surrounding and/or intermingled with the root structure of the plant 2. The ultraviolet sources 14A can generate ultraviolet radiation having a wavelength or combination of wavelengths suitable for combatting mildew, disinfecting water from bacteria, and/or the like.

Figure 6B:
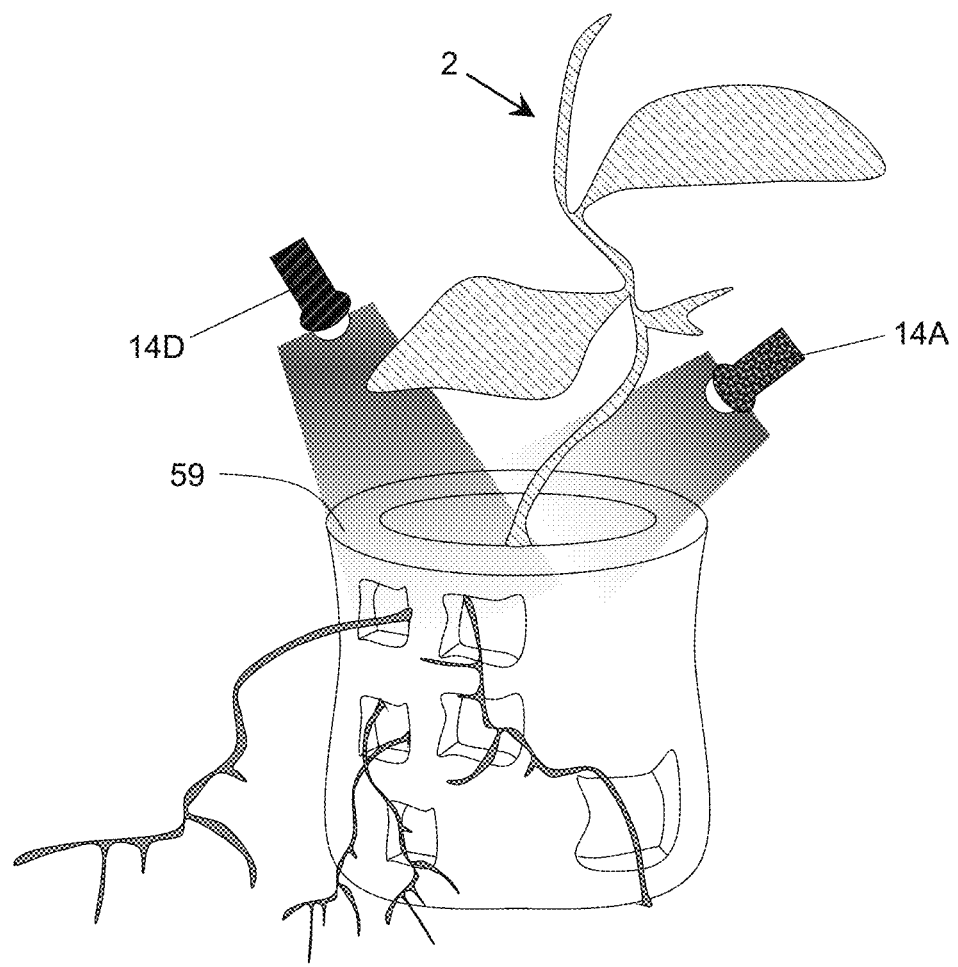

FIG. 6B shows another illustrative configuration of I/O devices of a control system for treating roots of a plant according to an embodiment. Such a configuration also can be utilized, for example, in plants grown hydroponically, without the presence of soil. In this case, an enclosure 59 is included, which can include various openings through which the roots of the plant 2 can grow. The root treatment system can include an ultraviolet source 14A and a blue-UV source 14D. The sources 14A, 14D can be located to radiate the enclosure 59 and/or the roots of the plant 2 in order to reduce mildew within the roots of the plant.

In an embodiment, the enclosure 59 comprises a surface having photocatalytic properties. For example, illustrative surfaces can comprise titanium dioxide ($TiO_2$), copper, silver, copper/silver particles, silver nanocomposites such as Ag—AgCl/$TiO_2$ xerogels, zeolite Ag—AgBr, $ZnO_2$, Ag—$ZnO_2$, and/or the like. In an embodiment, the ultraviolet source 14A can emit UV-A light directed onto the photocatalytic surface(s) of the enclosure 59 to promote production of hydroxyl in order to disinfect roots containing mildew. The blue-UV source 14D can emit blue-UV light that is directed onto the roots of the plant 2 for producing reactive oxygen species (ROS). In an embodiment, an intensity and/or duration of these radiation sources 14A. 14D is selected to reduce mildew without significantly affecting the health of the plant 2.

It is understood that the control system described herein includes various electronic drivers, power sources, and/or other mechanisms, which enable the selective operation of (e.g., application of power to) the I/O devices described herein. Such features have not been particularly shown and described in order to clearly describe unique features of the invention. Additionally, a control system described herein can incorporate any combination of various types of structures and mechanisms to support, locate, and/or relocate I/O devices around plants growing in a cultivated area. For example, an embodiment of the control system can utilize movable and rotatable robotic arms to locate I/O devices in various parts of a plant.

Figure 7:
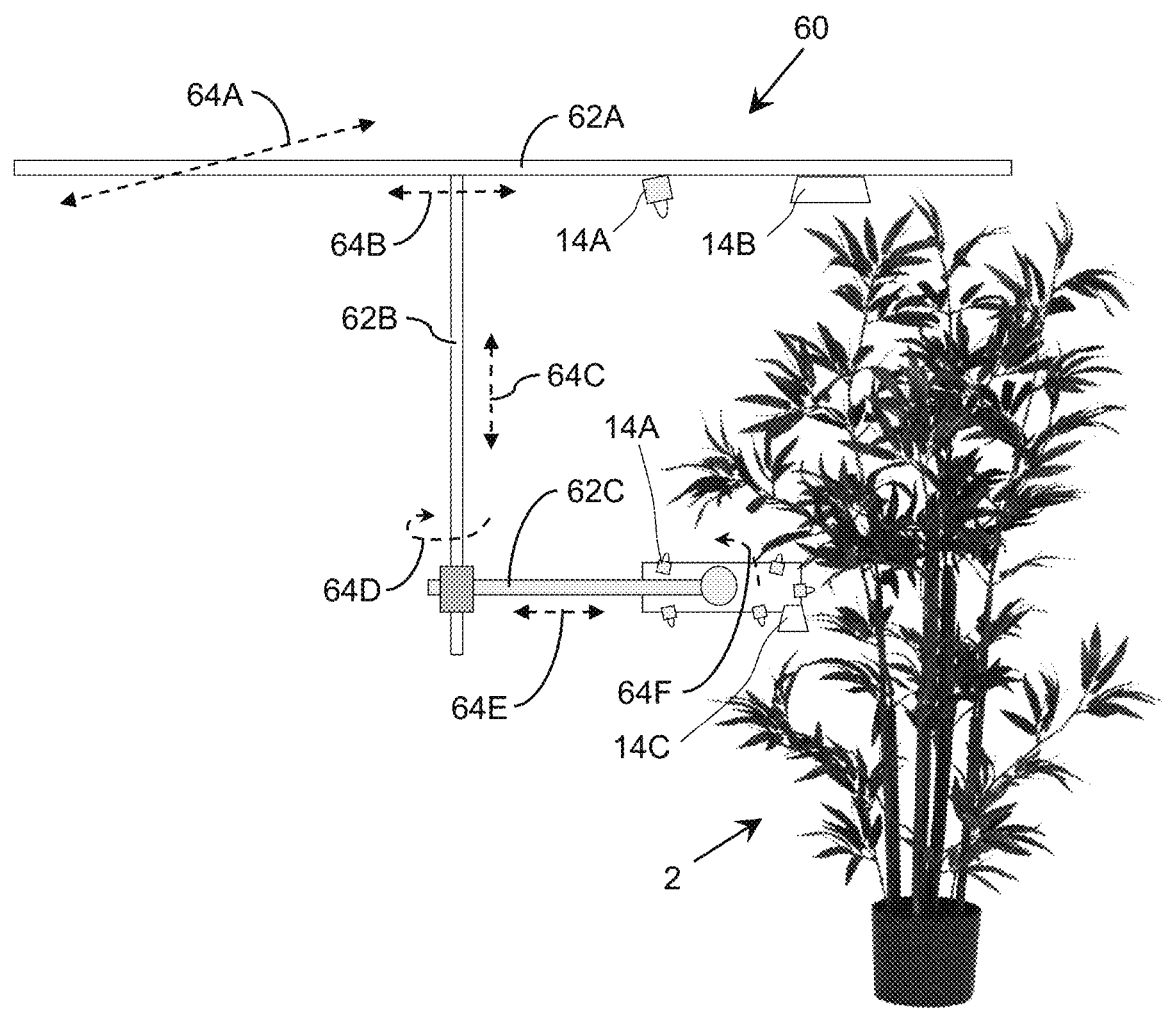
FIG. 7 shows an illustrative configuration of I/O devices and support structure for a control system described herein according to an embodiment.

To this extent, FIG. 7 shows an illustrative configuration of I/O devices and support structure for a control system described herein according to an embodiment. In this case, the support structure includes a movable arm 60, which can be operated to deliver ultraviolet radiation (and/or other treatment described herein) to various parts of the plant 2. The movable arm 60 can include several segments 62A-62C, each of which is capable of independent movement in one or more directions 64A-64F using any type of mechanism known the art. While only some directions of movement 64A-64F are indicated, it is understood that each segment 62A-62C can be configured to move in any combination of multiple degrees of freedom. As illustrated, one or more of the segments can include one or more I/O devices, such as an ultraviolet source 14A, sensor 14B (e.g., an imaging device), and/or environmental device 14C (e.g., an air jet). The control system can operate the movable arm 60 and the I/O devices 14A-14C included thereon to detect mildew and deliver ultraviolet radiation to various parts of the plant 2 (e.g., various leaf surfaces) affected by the mildew.

As discussed herein, a structure including one or more of the I/O devices can be relocatable within a cultivated area. In an embodiment, such a structure can be located on a robotic device, which can comprise a wheeled device for moving to different locations of a cultivated area. In another embodiment, the structure can be located on a drone, which can carry the I/O devices and hover in a desired location over the cultivated area.

As discussed herein, one or more attributes of the ultraviolet light used in treating a plant can vary based on the plant and/or a maturity (e.g., stage of life) of the plant. To this extent, an embodiment of the control system can adjust the spectral power distribution based on the type of plant being treated and/or the stage of life of the plant. For example, as illustrated in FIG. 8A, during an initial stage of life of the plant, the plant can be irradiated with a milder ultraviolet radiation having a larger wavelength, lower intensity, and lower overall dose. As the plant grows larger (e.g., matures), the radiation can be adjusted accordingly (e.g., shorter wavelength, higher intensity, and higher overall dose). In an embodiment, the radiation for the seedling is in a range of 270 to 310 nanometers and the radiation for the mature (pre-harvest) plant has a wavelength at least ten percent lower than that used for the seedling.

Similarly, a position and/or direction of the ultraviolet radiation can be adjusted according to a maturity of the plant. For example, for a seedling (or seed), the ultraviolet radiation can be delivered downward from a top of the leaves. As the plant matures, the position and/or direction from where the ultraviolet radiation is delivered can be adjusted, e.g., to accommodate illumination from below the leaves, onto a root structure or ground near the base of the plant, and/or the like. In a more particular embodiment, the control system can determine a set of target ultraviolet characteristics (wavelength, intensity, dose, direction, position, and/or the like) for a plant and a corresponding maturity of the plant using a feedback process described herein. In this case, the control system can store the parameters used for the ultraviolet radiation and/or additional environmental parameters, along with any affects (adverse or positive) and evaluate the information to refine and improve the target attributes used in the ultraviolet treatment and/or growth environment for different types of plant during different growth periods.

An embodiment of the control system described herein can include various ultraviolet sources configured to emit ultraviolet radiation of several distinct wavelengths. The particular wavelength(s) emitted in treating a plant also can be selected based on a purpose of the ultraviolet treatment. For example, FIG. 8B shows different affects that ultraviolet light of differing wavelengths can produce in plants according to embodiments. In this case, the control system can include ultraviolet source(s) that emit ultraviolet radiation in a range of 250-290 nanometers (260-285 in a more particular embodiment) to combat mildew by directly damaging the mildew DNA and thus suppressing mildew growth. Additionally, the control system can include ultraviolet source(s) that emit ultraviolet radiation in a range of 280-310 nanometers (280-290 nanometers in a more particular embodiment), which can stimulate the plant defense system against external stresses, can increase antioxidants in some plants, increase vitamin D in some plants, increase flavonoids in certain plants, prolong food preservation during storage, and/or the like. In a more particular embodiment, a set of ultraviolet sources can emit ultraviolet radiation having a peak wavelength of 295 nm with a FWHM of about 10 nm to increase flavonoid content in a plant. Furthermore, the control system can include ultraviolet source(s) that emit ultraviolet and/or visible radiation in a range of 350-430 nanometers (blue-UV radiation in a range of 380-420 nanometers in a more particular embodiment), which can improve plant coloring of certain plants (such as flowers), improve plant aroma, increase flavor, and/or the like.

Figure 9:
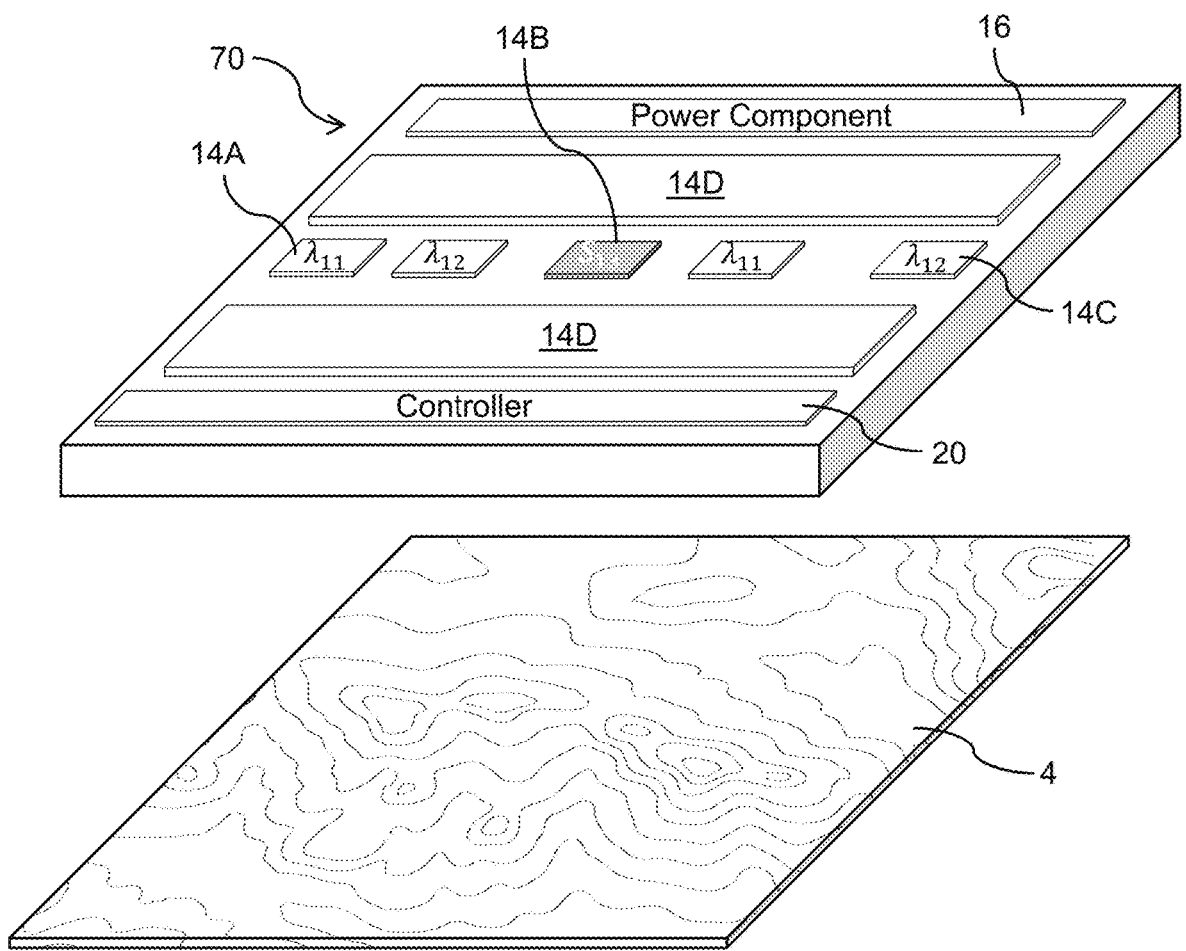
FIG. 9 shows an illustrative control system for irradiating a plant surface according to an embodiment.

It is understood that a control system described herein can include combinations of various radiation sources and/or sensors for use in treating a plant 2. To this extent, FIG. 9 shows an illustrative control system 70 for irradiating a plant surface 4 according to an embodiment. The control system 70 can include a first set of ultraviolet sources 14A, a second set of radiation sources 14D, and a third set of radiation sources 14C for irradiating the surface 4. It is understood that the sets of radiation sources 14A, 14C, 14D, along with other features of the control system 70, can be located at any location on the surface of the control system 70 and the depiction in FIG. 9 is only an example of one configuration. To this extent, it is understood that the particular arrangement, sizes, quantities, etc., of the illustrative components of the control system 70 depicted in FIG. 9 is only illustrative of various arrangements, sizes, quantities, etc., of the components.

In an embodiment, the first set of ultraviolet sources 14A can emit radiation having a peak wavelength in a range of approximately 250 nm to approximately 290 nm. In a more specific embodiment, the first set of radiation sources 14A can operate in the wavelength range of approximately 270 nm to approximately 290 nm. In an embodiment, the second set of radiation sources 14D can comprise blue-UV sources 14D, which can operate in the blue-UV wavelength range of 380-420 nm.

In an embodiment, the third set of radiation sources 14C can include sources of fluorescent radiation. In an embodiment, the third set of radiation sources 14C can include visible radiation sources, such as incandescent, fluorescent, laser, solid state, and/or the like, that operate at least partially in the wavelength range of 400 nm to 700 nm. For example, the third set of radiation sources 14C can include a visible source of collimated light capable of irradiating the surface 4 at a set of angles. In an embodiment, the third set of radiation sources 14C can include infrared radiation sources, such as blackbody, solid state, and/or the like, that emit radiation that is in the wavelength range of 700 nm to 1 millimeter (mm).

Regardless, it is understood that when a set of radiation sources 14A, 14C, 14D includes multiple radiation sources, the set of radiation sources 14A, 14C, 14D can include radiation sources that emit radiation of a plurality of distinct wavelengths. To this extent, in another embodiment, one or more of the second set of radiation sources 14D can comprise a blue-UV source while one or more of the second set of radiation sources 14D comprises a UV-A source. In a more particular embodiment, the UV-A source emits radiation have a peak wavelength in a range of approximately 340 nm to approximately 380 nm.

In an embodiment, the radiation sources 14D comprise high intensity wide coverage sources capable of continuous operation in an efficient matter over a large stretch of time. In a more particular embodiment, the radiation sources 14D can operate continuously for a duration of several days. Prolonged exposure to blue-UV radiation results in sterilization due to generation of reactive oxygen species (ROS). ROS are chemically reactive chemical species that contain oxygen. The ROS can disrupt the proliferation of microorganisms on the surface 4 by binding to and oxidizing the microorganisms.

In an embodiment, each of the radiation sources in the first set of radiation sources 14A can irradiate a different location of the surface 4. In another embodiment, the first set of radiation sources 14A can all irradiate different locations on the surface 4 but with relatively uniform radiation. In another embodiment, more than one ultraviolet radiation source in the first set of ultraviolet radiation sources 14A can irradiate a single location on the surface 4, with each ultraviolet radiation source operating at a different wavelength and/or intensity.

In an embodiment, each of the radiation sources in the first set of radiation sources 14A can operate at a specific wavelength within a range of 250 nm to 360 nm. In an embodiment, the wavelength range can be selected to be significantly narrower, depending on the type of microorganisms being sterilized. For example, in an embodiment, the wavelength range can extend from 270 nm to 320 nm. In another embodiment, depending on the surface 4, the wavelength range can extend from 280 nm to 300 nm, or from 260 nm to 280 nm. In one embodiment, the radiation sources 14A can have a peak wavelength that ranges from 270 nm to 300 nm. In another embodiment, the ultraviolet radiation sources can have a peak wavelength of 295 nm with a full width half maximum of 10 nm. It is understood that these ranges are only examples and the wavelength range for the ultraviolet radiation sources in the first set of radiation sources 14A can be any wavelength range within the range of 250 nm to 360 nm.

Optical elements can be included to facilitate the efficiency of radiation. In an embodiment, the first set of radiation sources 14A can include a set of reflective optical elements in order to focus the ultraviolet radiation to specific locations on the surface 4 In an embodiment, the set of reflective optical elements can include one or more of: a lens, a set of lenses, a parabolic reflector, a wave-guiding structure, and/or the like. In an embodiment, the optical elements can include UV transparent material.

It is understood that one or more of the sets of radiation sources 14A, 14C, 14D can produce a distributed intensity over one or more areas of the surface 4 that is located a distance away from the control system 70. In an embodiment, the distance between the control system 70 and the surface 4 can range from a few centimeters to several meters. In an embodiment, irradiation of a location defines a region of the surface 4 that is impinged by radiation, wherein the intensity of radiation deposited at the boundary of the region is at most 10% of the intensity of light deposited at the center of the region. It is understood that the position of irradiated locations can be adjusted to result in separate locations over the surface 4, wherein separate means that the intensity of radiation between each of the locations is no larger than 10% of the intensity in the center of the locations. In addition, these locations of irradiation can be designed to have relatively uniform radiation, with radiation intensity varying through the location by no more than several times (e.g., a factor of three or less) between any two points within the location.

Furthermore, the control system 70 can include a sensor 14B (e.g., a visual camera) capable of detecting the intensity of the reflected light at the set of angles. Although only one sensor 14B is shown on the control system 70, it is understood that the control system 70 can include any number of sensors 14B. To this extent, the control system 70 can include one or more of various types of sensors 14B. The set of sensors 14B can be configured to measure a plurality of conditions associated with the radiation emitted from any of the sets of radiation sources 14A, 14C, 14D or the surface 4. The set of sensors 14B can include one or more sensors to detect visible radiation, blue-UV radiation, UV radiation (e.g., UV-A, UV-B, UV-C, and/or the like), infrared radiation, chemical fluorescence, and/or the like.

In an embodiment, the set of sensors 14B can include one or more sensors configured to detect fluorescent light radiated by the microorganisms on the surface 4. In an embodiment, the set of sensors 14B can include one or more fluorescent radiation sensors configured to detect fluorescent radiation induced on the surface 4 by one or more of the sets of radiation sources 14A, 14C, 14D. In an embodiment, the third set of radiation sources 14C can include one or more visible radiation sources and the set of sensors 14B can include a visual camera configured to monitor the conditions of the surface 4. For example, the visual camera can detect changes in the surface appearance (e.g., changes in color, mildew growth, presence of dirt particles, changes in reflective or scattering properties of the surface, and/or the like). In an embodiment, the set of sensors 14B can also include environmental condition sensors, such as a temperature sensor, a humidity sensor, a gas sensor, and/or the like.

The control system 70 can include a controller 20 that is configured to control and/or adjust operation of the set of radiation sources 14A, 14C, 14D and the set of sensors 14B. In an embodiment, the controller 20 can be implemented as a computer system described in conjunction with FIG. 1. The controller 20 can control and/or adjust the set of radiation sources 14A, 14C, 14D according to a plurality of radiation settings. The plurality of radiation settings can be selected based upon various environmental conditions in which the surface 4 is located, various attributes regarding the surface 4 and/or the area surrounding the surface 4 determined by data acquired by the set of sensors 14B, and/or the like. For example, the controller 20 can determine a set of attributes regarding the surface 4 and/or the area surrounding the surface 4 and adjust the plurality of radiation settings of the set of radiation sources 14A, 14C, 14D and the set of sensors 14B to achieve a target set of attributes for the surface 4 and/or the area surrounding the surface 4.

In one embodiment, the controller 20 can detect changes imparted to the surface 4 from irradiation by one or more of the radiation sources 14A, 14C, 14D as a function of data fed back from the sensor 14B. In particular, the controller 20 can detect the changes as a function of the data associated with the irradiation by the first set of radiation sources 14A and the second set of radiation sources 14D, and the data associated with environmental conditions surrounding the surface 4. In one embodiment, the data associated with the irradiation can include the intensity, dosage, duration, wavelength, the type of radiation emitted from the first set of radiation sources 14A and the second set of radiation sources 14D, and the frequency of irradiation. In an embodiment, the changes that can be detected by the controller 20 can include change in color of the surface 4, change in fluorescence from the surface 4, change in reflective properties of the surface 4, and/or the like.

The controller 20 can detect the changes imparted to the surface 4 from the data obtained from the sensor 14B using any solution. For example, in an embodiment, using visual means can include a source of visible radiation (e.g., such as the radiation sources 14C), and a camera sensitive to visible radiation (e.g., such as the sensor 14B). The camera can acquire image data of the surface 4 at a first instance of time and at a later instance of time under similar lighting conditions, assuming that the surface 4 has not moved significantly or otherwise been physically altered. The controller 20 can compare the image data to determine changes in color and/or surface optical properties. The changes in color or a fluorescent signal can provide information regarding an overall microbial growth present on the surface 4. Fluorescent radiation sources and fluorescence sensors can be utilized to acquire information regarding changes of the surface 4 related to accumulation of fluorescent bacteria. Similar to the visual source and camera, the fluorescent sources and sensors can acquire data at set instances of time, which the controller 20 can compare at such different instances.

As illustrated, the control system 70 can include a power source 16 that is configured to power the radiation sources 14A, 14C, 14D, the sensors 14B, the controller 20, etc. In one embodiment, the power source 16 can take the form of an interface to a wall socket for providing electrical power from a building, electrical grid, etc. In an embodiment, the power source 16 can comprise a portable power source, which can include one or more batteries, a vibration power generator that can generate power based on magnetic inducted oscillations or stresses developed on a piezoelectric crystal, etc. In another embodiment, the power source 16 can include a super capacitor that is rechargeable. Other power components that are suitable for use as the power source 16 can include a mechanical energy to electrical energy converter such as a piezoelectric crystal, and a rechargeable device.

The aforementioned components of the control system 70 are only illustrative of one possible configuration. It is understood that the control system 70 can utilize other components in addition to, or in place of those shown and described herein. These additional components can perform similar functions to those described herein or different ones. The type of additional components and functionalities that are performed will depend on the type of surface 4 and the result that is desired through irradiation by the radiation sources 14A, 14C, 14D.

Figure 10A:
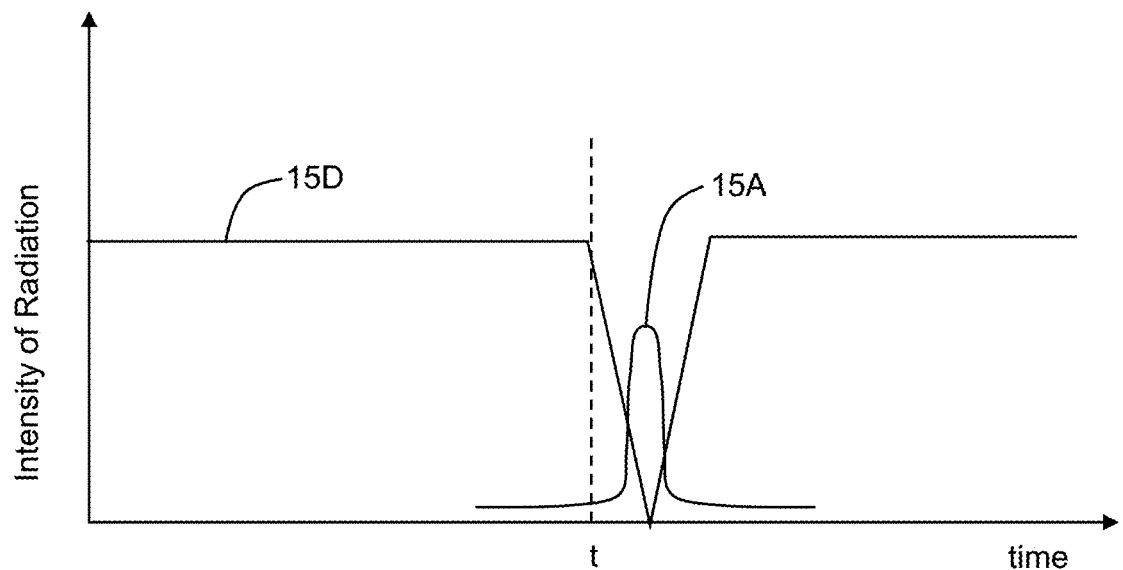
FIGS. 10A and 10B show an illustrative operation scenario in which a first set of radiation sources and a second set of radiation sources are operated as a function of time according to an embodiment.
Figure 10B:
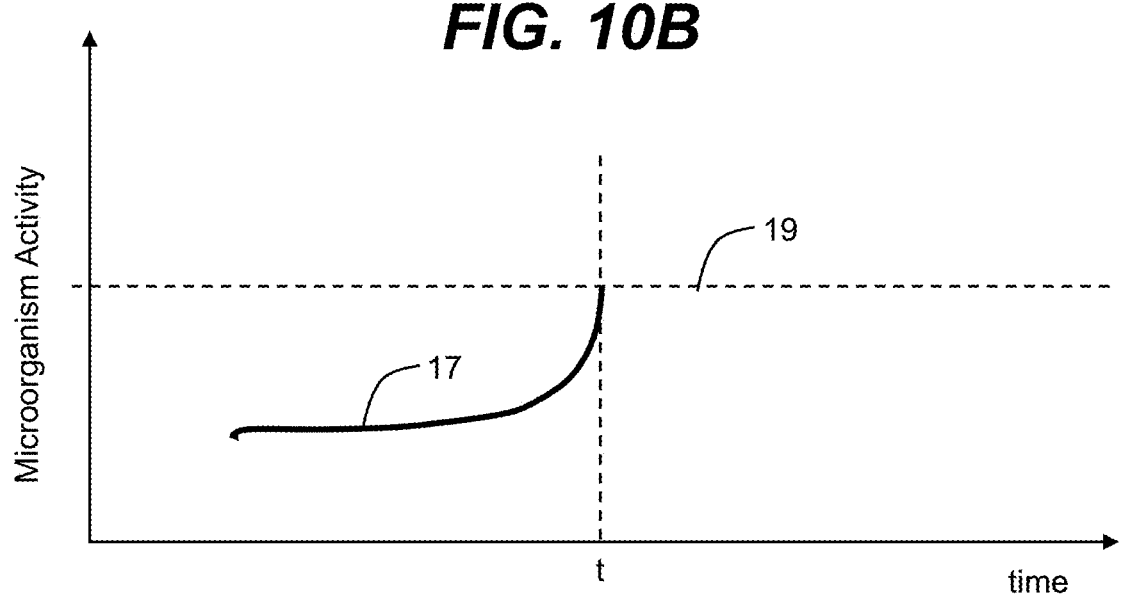

FIGS. 10A and 10B show an illustrative operation scenario in which a first set of radiation sources and a second set of radiation sources, such as the first set of radiation sources 14A and the second set of radiation sources 14D shown in FIG. 1 and FIG. 9, are operated as a function of time according to an embodiment. As shown in FIG. 10A, the second set of radiation sources 14D can initially emit blue-UV radiation at a constant intensity 15D.

During this time, the control system can determine whether any contamination is present (e.g., a level of microorganism activity) on the surface 4 being illuminated. For example, the control system can evaluate an amplitude of a fluorescent signal sensed by a fluorescent sensor, visual data from a visual camera, and/or the like. To this extent, the blue-UV radiation can elicit a fluorescent signal when microbial activity is present on the surface 4. Alternatively, the surface 4 can be periodically irradiated with a radiation source 14C (FIG. 1) that is capable of eliciting a fluorescent signal if microbial activity is present. Regardless, the control system (e.g., a computer system 20 shown in FIG. 1) can determine a level of contamination and/or an amount of microbial activity based on an amplitude of the fluorescent signal sensed by a fluorescent sensor as indicated by reference 17 in FIG. 10B. The surface 4 can be irradiated by the blue-UV radiation over a prolonged period of time that ranges from tens of minutes to tens of hours while the control system periodically evaluates a level of a fluorescent signal to determine the level of microorganism activity. To this extent, the control system can periodically operate the fluorescence sensor to monitor the amount of contamination present on the surface 4.

In this example, FIG. 10B shows a sharp increase in the growth of microorganism activity as noted by reference element 17. At time t, the level of microorganism activity crosses a predetermined contamination threshold 19 indicative of a need for more intense ultraviolet irradiation treatment due to rapid growth of microbial activity. In response, as shown in FIG. 10A, the control system can operate the first set of ultraviolet radiation sources 14A to emit ultraviolet radiation 15A (e.g., UV-C radiation) to perform the more intense ultraviolet irradiation treatment at a short burst of intensity that lasts at most a few minutes. In this manner, ultraviolet radiation 15A generated by the first set of ultraviolet radiation sources 14A can bring the microbial activity within appropriate limits by rapidly suppressing microbial activity on the surface 4. The blue-UV radiation 15D emitted by the second set of radiation sources 14D can be used to maintain microbial activity within limits over an extended period of time, while the ultraviolet radiation 15A emitted by the first set of radiation sources 14A can be designed to rapidly suppress microbial activity.

While shown and described herein as a control system for use while growing plant(s) in a cultivated area, such as a greenhouse, it is understood that aspects of the invention further provide various alternative embodiments. For example, in one embodiment, the control system described herein can be used to combat mildew and/or other parasitic attacks, in produce after harvesting, during a preservation stage. Similarly, the control system described herein can be configured to treat (e.g., disinfect) one or more components utilized in the cultivated area. For example, the control system can be configured to treat a water source/water used for watering the plants.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:
1. A system for managing plant growth, the system comprising:
   a plurality of radiation sources, wherein the plurality of radiation sources are configured to emit radiation having a plurality of distinct peak wavelengths;

a set of sensors for acquiring plant data for at least one plant surface of the plant, wherein the plant data includes data regarding a fluorescent signal received from the plant;

means for delivering radiation to the at least one plant surface of the plant, wherein the means for delivering includes at least one relocatable component; and a control system for controlling mildew and/or bacteria on the plant, wherein the controlling includes:
locating the at least one relocatable component to enable radiation to be directed to the at least one plant surface;
operating at least one of the plurality of radiation sources to illuminate the at least one plant surface with radiation having a first peak wavelength configured to induce a fluorescent response by mildew and/or bacteria;
evaluating the plant data acquired by the set of sensors to determine a presence of mildew and/or bacteria on the at least one plant surface; and
operating at least another one of the plurality of radiation sources to irradiate the at least one plant surface with ultraviolet radiation having a second peak wavelength distinct from the first peak wavelength in response to determining the presence of mildew and/or bacteria on the at least one plant surface.

2. The system of claim 1, further comprising a set of environmental devices, wherein the control system is further configured to selectively operate the set of environmental devices to affect a growth environment of the plant.

3. The system of claim 2, wherein the set of environmental devices includes a water source and an artificial lighting source.

4. The system of claim 2, wherein the set of environmental devices includes at least one of: a visible light source or an infrared light source.

5. The system of claim 2, wherein the set of environmental devices includes at least one of: a humidifier, a dehumidifier, a gas source, or a chemical treatment source.

6. The system of claim 1, wherein the at least one of the plurality of radiation sources emits blue-UV radiation and wherein the at least another one of the plurality of radiation sources emits UV-C radiation.

7. The system of claim 1, further comprising an enclosure including a plurality of openings through which roots of the plant have grown, the enclosure including at least one photocatalytic surface, wherein the operating includes irradiating the at least one photocatalytic surface.

8. The system of claim 1, wherein the control system adjusts at least one attribute of the ultraviolet radiation emitted by the at least another one of the plurality of radiation sources based on a maturity of the plant.

9. The system of claim 8, wherein the control system adjusts the second peak wavelength to emit ultraviolet radiation having a shorter wavelength as the plant is more mature.

10. The system of claim 1, wherein the means for delivering includes at least one air source for generating a wind to affect a location of at least a portion of the plant during operation of at least one of: the set of sensors or a radiation source of the plurality of radiation sources.

11. A farmed area comprising:
a plurality of plants; and
a system for managing growth of the plurality of plants, the system comprising:
a plurality of radiation sources, wherein the plurality of radiation sources are configured to emit radiation having a plurality of distinct peak wavelengths;
means for delivering the radiation to a selected plant surface of the at least one of the plurality of plants, wherein the means for delivering includes at least one relocatable component;
a set of sensors for acquiring plant data for at least one plant surface of the at least one of the plurality of plants, wherein the plant data includes data regarding a fluorescent signal received from the at least one of the plurality of plants; and
a control system for controlling mildew and/or bacteria on the at least one of the plurality of plants, wherein the controlling includes:
operating at least one of the plurality of radiation sources and the means for delivering to illuminate the at least one plant surface with radiation having a first peak wavelength configured to induce a fluorescent response by mildew and/or bacteria;
evaluating the plant data acquired by the set of sensors to determine a presence of mildew and/or bacteria on the at least one plant surface; and
operating at least another one of the plurality of radiation sources to irradiate the at least one plant surface with radiation having a second peak wavelength distinct from the first peak wavelength in response to determining the presence of mildew and/or bacteria on the at least one plant surface.

12. The farmed area of claim 11, wherein the farmed area is within a greenhouse.

13. The farmed area of claim 11, wherein the means for delivering includes a plurality of movable plant treatment components, each plant treatment component including:
a subset of the plurality of radiation sources;
a subset of the set of sensors; and
an onboard control device for controlling the subset of the plurality of radiation sources and the subset of the set of sensors and for communicating with the control system, wherein the control system provides treatment instructions to the onboard control device.

14. The farmed area of claim 13, wherein at least one of the plurality of movable plant treatment components is relocatable to any of a plurality of regions of the farmed area.

15. The farmed area of claim 13, wherein at least one of the plurality of movable plant treatment components further includes a set of environmental devices, wherein the onboard control device is further configured to selectively operate the set of environmental devices to affect a growth environment of the plant.

16. The farmed area of claim 13, further comprising a set of environmental control components, wherein the control system adjusts operation of the set of environmental control components to coordinate with operation of the plurality of movable plant treatment components.

17. A system for managing plant growth, the system comprising:
a control system for managing the plant growth, wherein the managing includes managing evaluation of a presence of mildew and/or bacteria on at least one plant in the cultivated area and treatment of the mildew and/or bacteria when evaluated as being present; and
at least one movable plant treatment component, the at least one moveable plant treatment component including:

a plurality of radiation sources, wherein the plurality of radiation sources are configured to emit radiation having a plurality of distinct peak wavelengths;

a set of sensors for acquiring plant data for at least one plant surface of a plant, wherein the plant data includes data regarding a fluorescent signal received from the at least one of the plurality of plants; and an onboard control device for controlling mildew and/or bacteria on the at least one of the plurality of plants, wherein the controlling includes:

controlling at least one of the plurality of radiation sources and the set of sensors to acquire data regarding the fluorescent signal received from the at least one of the plurality of plants;

processing the plant data to determine a presence of mildew and/or bacteria on the at least one of the plurality of plants;

communicating with the control system in response to determining the presence of mildew and/or bacteria;

receiving treatment instructions for treating the mildew and/or bacteria determined to be present on the at least one plant using at least another one of the plurality of radiation sources; and treating the mildew and/or bacteria according to the treatment instructions.

18. The system of claim 17, further comprising a set of environmental control components, wherein the managing further includes operating the set of environmental control components to affect a set of attributes of a growth environment for the plants, and wherein the control system adjusts operation of the set of environmental control components to coordinate with operation of the at least one movable plant treatment component.

19. The system of claim 17, further comprising a set of plant growth components, wherein a plant growth component includes a set of I/O devices for affecting a growth environment of a plant to promote growth, wherein the control system further manages operation of the set of plant growth components.

20. The system of claim 19, wherein the control system directs operation of at least one of the set of plant growth components on the at least one plant after the mildew and/or bacteria treatment.

* * * * *